(12) United States Patent
Rys

(10) Patent No.: US 10,981,002 B2
(45) Date of Patent: Apr. 20, 2021

(54) INTERCOSTAL MUSCLE FIXATION FOR AN IMPLANTED MEDICAL DEVICE

(71) Applicant: Verily Life Sciences LLC, South San Francisco, CA (US)

(72) Inventor: Ken Rys, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 170 days.

(21) Appl. No.: 15/927,600

(22) Filed: Mar. 21, 2018

(65) Prior Publication Data

US 2018/0272122 A1 Sep. 27, 2018

Related U.S. Application Data

(60) Provisional application No. 62/474,684, filed on Mar. 22, 2017, provisional application No. 62/475,260, filed on Mar. 23, 2017.

(51) Int. Cl.
*A61N 1/00* (2006.01)
*A61N 1/05* (2006.01)
(Continued)

(52) U.S. Cl.
CPC .......... *A61N 1/059* (2013.01); *A61N 1/37211* (2013.01); *A61N 1/37518* (2017.08);
(Continued)

(58) Field of Classification Search
CPC .. A61N 1/059; A61N 1/05–06; A61N 1/3605; A61N 1/37211; A61N 1/37518;
(Continued)

(56) References Cited

U.S. PATENT DOCUMENTS

| 7,369,901 B1 | 5/2008 | Morgan et al. |
| 2005/0119694 A1 | 6/2005 | Jacobs et al. |

(Continued)

FOREIGN PATENT DOCUMENTS

WO 2012057862 A1 5/2012

OTHER PUBLICATIONS

International Application No. PCT/US2018/023607, "International Search Report and Written Opinion", dated Jun. 11, 2018, 12 pages, European Patent Office.

(Continued)

*Primary Examiner* — Scott M. Getzow
(74) *Attorney, Agent, or Firm* — Kilpatrick Townsend & Stockton LLP

(57) ABSTRACT

An implantable medical device that can include a main body having a tissue-contacting surface comprising a first edge and a second edge, an elongated shaft coupled at or near a first edge of the main body, and an anchoring feature extending from a second end of the elongated shaft. The elongated shaft can have a long axis that extends from a first end of the elongated shaft to a second end of the elongated shaft. The elongated shaft can be oriented such that the second end is positioned above the tissue-contacting surface and an angle between the long axis of the elongated shaft and the tissue-contacting surface is an acute angle. The device can further include an opposing elongated shaft coupled at or near a second edge of the main body.

20 Claims, 12 Drawing Sheets

(51) Int. Cl.
  *A61N 1/375* (2006.01)
  *A61N 1/372* (2006.01)
  *A61N 1/378* (2006.01)
  *A61B 5/00* (2006.01)
  *A61B 5/145* (2006.01)
  *A61N 1/36* (2006.01)

(52) U.S. Cl.
  CPC ......... *A61B 5/0059* (2013.01); *A61B 5/14532* (2013.01); *A61N 1/36* (2013.01); *A61N 1/378* (2013.01); *A61N 1/3756* (2013.01)

(58) Field of Classification Search
  CPC ........ A61N 1/36; A61N 1/3756; A61N 1/378; A61B 5/14532; A61B 5/0059
  See application file for complete search history.

(56) References Cited

U.S. PATENT DOCUMENTS

| 2007/0150034 | A1 | 6/2007 | Rooney et al. |
| 2009/0192381 | A1* | 7/2009 | Brockway ............ A61N 1/0504 600/373 |
| 2012/0197332 | A1 | 8/2012 | Peichel et al. |
| 2013/0192611 | A1 | 8/2013 | Taepke, II et al. |
| 2014/0163579 | A1* | 6/2014 | Tischendorf ....... A61N 1/36139 606/129 |
| 2020/0254249 | A1* | 8/2020 | Rondoni ............ A61N 1/37205 |

OTHER PUBLICATIONS

Walter et al., "Stimulating Multiple Respiratory Muscles With Intramuscular Permaloc Electrodes", J. Spinal Cord Med, v.33(2); Apr. 2010.

Micra Transcatheter Pacing System, http://www.medtronic.com/us-en/healthcare-professionals/products/cardiac-rhythm/pacemakers/micra-pacing-system.html (printed to PDF on Apr. 2, 2018) (Publication date N/A).

St. Jude Medical, "The Nanostim™ Leadless Pacemaker." (2013).

International Application No. PCT/US2018/023607, "International Preliminary Report on Patentability", dated Oct. 3, 2019, 8 pages.

\* cited by examiner

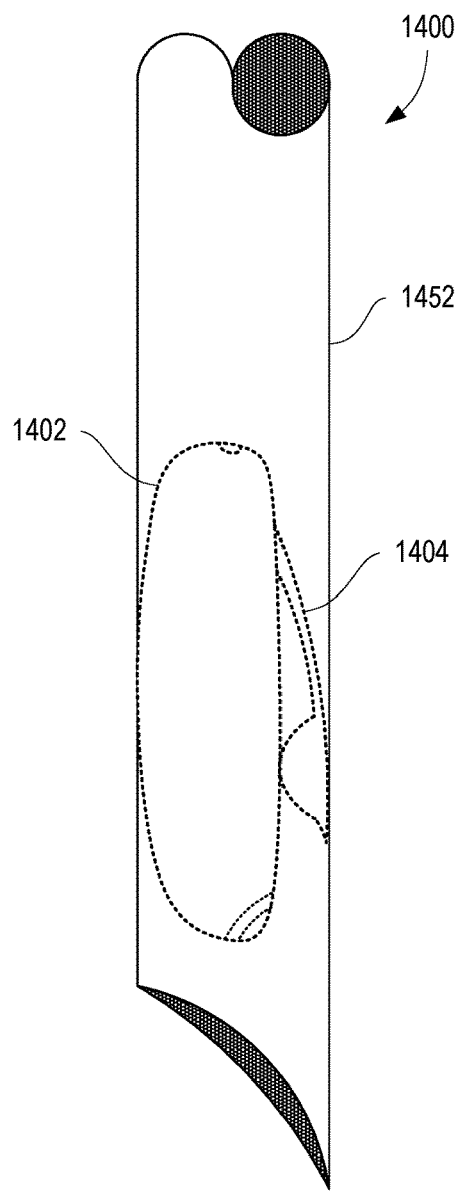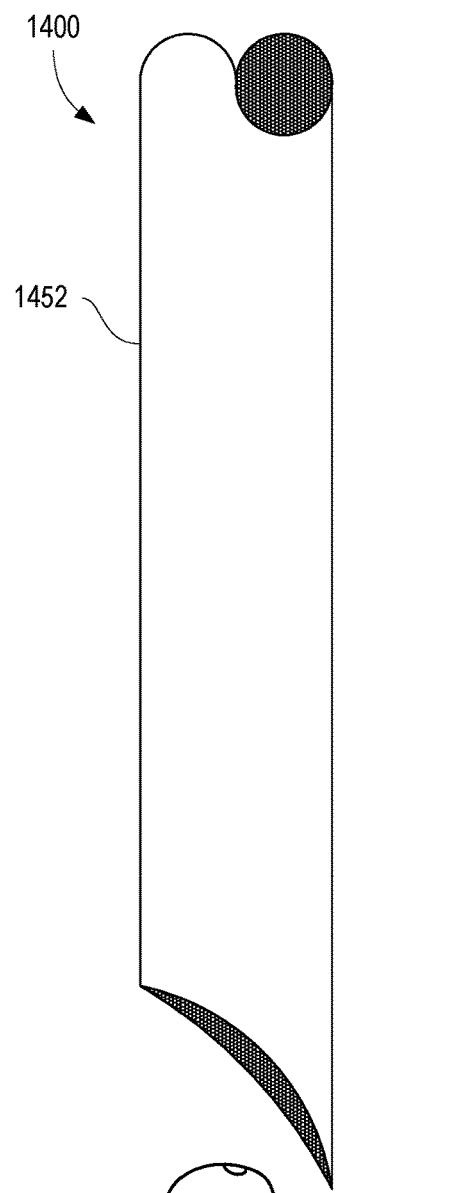
FIG. 14  FIG. 15

INTERCOSTAL MUSCLE FIXATION FOR AN IMPLANTED MEDICAL DEVICE

CROSS-REFERENCE TO RELATED APPLICATIONS

This application claims the benefit of and the priority to U.S. Provisional Application No. 62/474,684, filed on Mar. 22, 2017, and U.S. Provisional Application No. 62/475,260, filed on Mar. 23, 2017. Each of these applications is hereby incorporated by reference in its entirety for all purposes.

TECHNICAL FIELD

The present disclosure generally relates to medical devices and more specifically to implantable medical devices and techniques for fixing implantable medical devices to muscle tissue.

BACKGROUND

Implantable medical devices are a growing field of medical technologies for detecting, treating, or otherwise interacting with conditions within the body. Many types of implantable medical devices exist, including bioelectronic devices intended to detect or supply electrical stimulation to targeted tissue within the body.

Due to current design limitations, however, medical implants often require a lead that extends from a controller (e.g., a subcutaneous pulse generator) to the target tissue. The controller is often implanted in a subcutaneous pouch near the surface of the skin, while the lead travels from the controller to the target tissue. The implant site of the controller can often produce a cosmetically undesirable bulge and may require a large incision and pocket which can increase the risk of infection. Further, when intrathoracic tissue is targeted (e.g., the heart, the spleen, or nearby nerve tissue), the lead from the controller to the target tissue must cross through several body compartments. As each of these body compartments move relative to one another, the lead can undergo large, localized mechanical loads, which can lead to premature failure due to fatigue fracture. In some cases, leads can be passed through adjacent body compartments intravascularly, however such an intravascular approach can limit the possible target sites.

Some designs may attempt to address some issues using leadless devices, such as devices implanted entirely within the heart. However, such devices can have drawbacks associated with their design and form factor, such as only being able to target tissue at the implant site. Further, deep-organ implants suffer from other complications, such as the need for increased wireless communication power due to the deeper implant site.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Some embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

In some embodiments, an implantable medical device is provided that includes: a main body having a tissue-contacting surface comprising a first edge and a second edge, the tissue-contacting surface of the main body having a convex shape; an elongated shaft having a long axis that extends from a first end of the elongated shaft to a second end of the elongated shaft, wherein the elongated shaft includes a shaft-connection site that is at or near the first end and that is coupled to a surface-connection site of the main body, the surface-connection site of the main body being positioned at or near the first edge of the main body, wherein the elongated shaft is oriented such that: the second end is positioned above the tissue-contacting surface; and an angle between the long axis of the elongated shaft and the tissue-contacting surface is an acute angle; and an anchoring feature extending from the second end of the elongated shaft, the anchoring feature being configured to taper from an enlarged portion to a sharp distal tip, the sharp distal end being further from the second end than the enlarged portion, and a cross section of the enlarged portion of the anchoring feature being larger than a median cross section of the elongated shaft.

In some cases, the acute angle is between 10° and 50°. In some cases, the device further comprises an opposing elongated shaft that is coupled to the main body at or near the second edge of the main body. In some cases, a distal end of the opposing elongated shaft is also positioned above the tissue-contacting surface. In some cases, a second angle between a second long axis of the opposing elongated shaft and the tissue-contacting surface is also an acute angle. In some cases, the opposing elongated shaft is shorter than the elongated shaft. In some cases, the elongated shaft and the opposing elongated shaft are oriented such that the long axis of the elongated shaft and a second long axis of the opposing elongated shaft are in a same plane. In some cases, the opposing elongated shaft also includes an anchoring feature that tapers from an enlarged portion to a sharp distal tip.

In some cases, the device further comprises a second elongated shaft that is coupled to the main body at or near the first edge of the main body. In some cases, a second long axis of the second elongated shaft is parallel to the long axis of the elongated shaft. In some cases, a widest distance between the elongated shaft and the second elongated shaft is less than 18 mm. In some cases, the main body further comprises control circuity for generating an electrical stimulus. In some cases, the device further comprises a lead coupled to the control circuitry of the main body and configured to transmit electrical signals at a distal portion of the lead. In some cases, a contiguous feature includes the elongated shaft and the anchoring feature.

In some embodiments, a system is provided that include all or part of one or more implantable medical devices disclosed herein; and a delivery sheath that surrounds a circumference of the implantable medical device.

In some embodiments, a method of implanting a medical device is provided. The method comprises: inserting an implantable medical device into a delivery sheath in a compressed state such that the implantable medical device is at least partly wrapped, the implantable medical device comprising: a main body having a tissue-contacting surface comprising a first edge and a second edge, the tissue-contacting surface of the main body having a convex shape;

an elongated shaft having a long axis that extends from a first end of the elongated shaft to a second end of the elongated shaft, wherein the elongated shaft includes a shaft-connection site that is at or near the first end and that is coupled to a surface-connection site of the main body, the surface-connection site of the main body being at or near the first edge of the main body, the surface-connection site being positioned at or near the first edge; and an anchoring feature extending from the second end of the elongated shaft, the anchoring feature being configured to taper from an enlarged portion to a sharp distal tip, the sharp distal tip being further from the second end than the enlarged portion, and a cross section of the enlarged portion of anchoring feature being larger than a median cross section of the elongated shaft; guiding the at least partly wrapped implantable medical device to an implant site; deploying the implantable medical device from the delivery sheath, wherein deploying includes releasing the implantable medical device into a decompressed state, such that the elongated shaft is oriented such that: the second end is positioned above the tissue-contacting surface; and an angle between the long axis of the elongated shaft and the tissue-contacting surface is an acute angle; and inserting the elongated shaft into the implant site such that the anchoring feature attaches to a portion of the implant site.

In some cases, the implantable medical device further includes an opposing elongated shaft that is coupled to the main body at or near the second edge of the main body; and when the implantable medical device is in the decompressed state, a distal end of the opposing elongated shaft is positioned above the tissue-contacting surface at a second acute angle. In some cases, the method further comprises inserting the opposing elongated shaft into the implant site. In some cases, the elongated shaft and the opposing elongated shaft are inserted into the implant site at different times. In some cases, the elongated shaft and the opposing elongated shaft are different lengths.

BRIEF DESCRIPTION OF THE DRAWINGS

The specification makes reference to the following appended figures, in which use of like reference numerals in different figures is intended to illustrate like or analogous components.

FIG. 14 is a front view depicting an implantation kit containing an implantable medical device with an elongated shaft in a compressed position within a trocar according to certain aspects of the present disclosure.

FIG. 15 is a front view depicting the implantation kit of FIG. 14 with the elongated shaft of the medical device in a deployed position after exiting the trocar according to certain aspects of the present disclosure.

DETAILED DESCRIPTION

Figure 1:
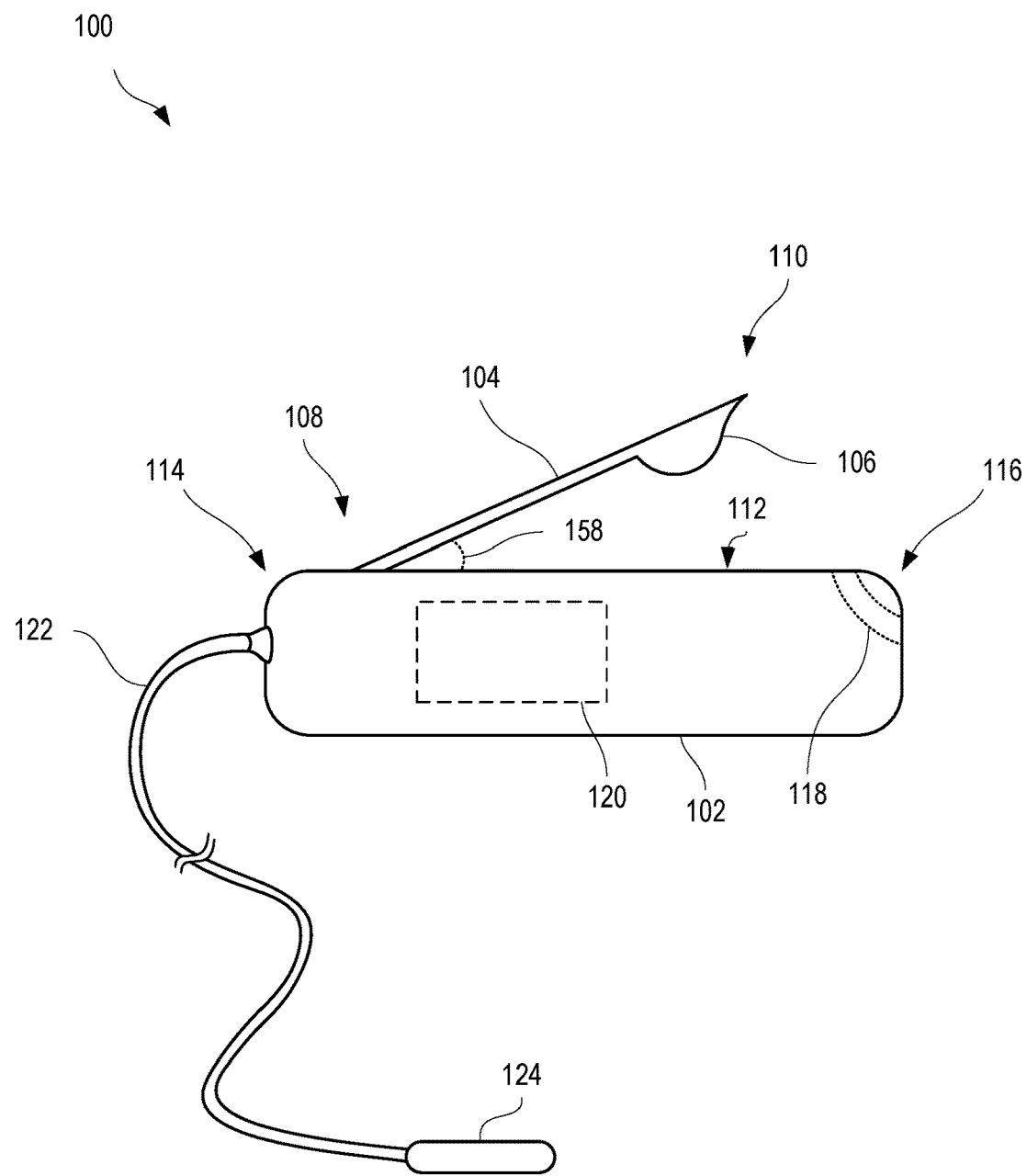
FIG. 1 is a schematic diagram depicting an implantable medical device having a main body with an elongated shaft according to certain aspects of the present disclosure.

Certain aspects and features of the present disclosure relate to an implantable medical device anchorable against muscle tissue, e.g., intercostal muscle tissue. The device can include one or more elongated shafts, extending from a main body, oriented to engage the intercostal muscle tissue and anchor the main body of the implantable medical device against the muscle tissue. Each elongated shaft can include a long axis that extends from a first end of the elongated shaft to a second end of the elongated shaft. Each elongated shaft can include a shaft-connection site that is at or near the first end (e.g., the end closest to the main body) and can be coupled to a surface-connection site of the main body. The surface-connection site of the main body can be positioned at or near an edge of main body (e.g., the first edge or the second edge). In some aspects, a position (e.g., of the surface-connection site) can be defined to be "near" a given edge of the main body when (for example) a distance between the position and the given edge is less than two, five, ten or twenty times a complementary distance that is between the position and an opposite edge of the main body. The elongated shaft can be oriented such that the second end (e.g., end further from the main body) is positioned above the tissue-contacting surface and an angle between the long axis of the elongated shaft and the tissue-contacting surface (e.g., an angle between the long axis and a projection of the long axis on the tissue-contacting surface) can be an acute angle. Each elongated shaft can also include an anchoring feature designed to inhibit removal of the elongated shaft from the muscle tissue. In some cases, the anchoring feature can extend from the second end of the elongated shaft and can taper from an enlarged portion to a sharp distal tip. In some cases, the sharp distal tip can be further from the second end than the enlarged portion. In some cases, the enlarged portion of the anchoring feature can have a cross section that is larger than a median cross section of the elongated shaft (e.g., such that a maximum or mean cross-sectional area or maximum or mean cross-sectional diameter of the enlarged portion is at least 100%, 150%, 200%, or 500% the median cross-sectional area or median cross-sectional diameter of the elongated shaft). In some cases, the sharp distal tip can initially pierce the muscle tissue. In some cases, the implantable medical device can include a suture hole positioned to inhibit removal of the elongated shaft from the muscle tissue when a suture is applied through the suture hole and the muscle tissue.

Certain aspects and features of the present disclosure also relate to an implantable medical device that can be anchored against intercostal muscle tissue using opposing elongated shafts, e.g., an elongated shaft and an opposing elongated shaft. The opposing elongated shafts can extend from each respective edge of the main body in opposing directions and be oriented to engage an implant site and anchor the main body of the implantable medical device against the implant site, e.g., the intercostal muscle tissue. The elongated shafts can each have a sharp distal tip for piercing the muscle tissue. At least a first elongated shaft can have sufficient flexibility to promote sufficient displacement of the main body of the medical device after insertion of the first elongated shaft, the displacement being sufficient to allow the opposing elongated shaft to be inserted into the muscle tissue while tension remains between the first and opposing elongated shafts sufficient to anchor the main body against the muscle tissue.

An implantable medical device according to certain aspects of the present disclosure can allow for reliable implantation of a medical device, such as a controller or a pulse generator, entirely within a single body compartment of the patient, such as entirely within the thorax. In some cases, instead of being located entirely within the thorax, an implantable medical device according to certain aspects of the present disclosure can be located entirely within the ventral cavity, the abdominal cavity, or any suitable cavity of a patient.

The implantable medical device can target nearby tissue (e.g., via onboard electrodes), or can use a lead to target distant tissue. For example, the implantable medical device can include a lead for targeting any tissue within reach. In some cases, the implantable medical device can be separate from the lead and can be removably attached (e.g., using clips) to the lead. In some cases, the implantable medical device can be integrated with the lead. In one embodiment, the implantable medical device is combined with a lead and is configured for implantation in a patient. It can be desirable to use an intrathoracic implantable medical device when targeting intrathoracic tissue, so as to avoid passing a lead through multiple body compartments. An implantable medical device according to certain aspects of the present disclosure can thus be especially suitable for targeting intrathoracic tissue, such as the nerve plexus about the splenetic artery. Certain aspects and features of the present disclosure can be especially suitable for targeting implant sites such as neural tissue within the thorax, e.g., neural tissue controlling intrathoracic organs (e.g., the spleen). An implantable medical device according to certain aspects of the present disclosure can thus be especially suitable for targeting upper abdominal tissue, in addition to or instead of intrathoracic tissue.

Any suitable implantable medical device can be used according to the present disclosure, including electrical, chemical, or other devices. In some cases, implantable medical devices can sense and/or deliver electrical stimuli using electrodes on the main body of the implantable medical device and/or through a lead using electrodes present at a distal end of the lead. In some cases, the techniques described herein can be especially suitable for medical devices that are electrical pulse generators. In some cases, implantable medical devices can sense and/or deliver chemicals, light, or other conditions and/or treatments using suitable equipment present on the main body of the implantable medical device and/or through a lead using suitable equipment present at a distal end of the lead. For example, an implantable medical device positioned against intercostal muscle tissue can provide glucose monitoring or monitoring of chemicals in or around the gastrointestinal tract.

Certain aspects of the present disclosure can allow a controller of an implantable medical device to be implanted at a relatively shallow location, facilitating transcutaneous wireless communication. Additionally, the shallow implant site afforded by the present disclosure can permit the use of a relatively small, low power antenna, at least as compared to a deep-organ implant (e.g., implant located entirely within the heart). This relatively shallow implant site within the thorax can provide benefits to device size (e.g., smaller suitable size) and recharge frequency (e.g., ability to function for longer periods of time before needing a recharge), at least as compared to a deep-organ implant. Additionally, because the implantable medical device can be implanted entirely within the thorax, the implantable medical device can be implanted without a subcutaneous bulge. Further, the lack of a subcutaneous pocket and ability for the implantable medical device to be implanted via laparoscopic technique can provide a much lower infection rate than conventional medical device implants (e.g., pulse generator implants).

In some cases, the relatively shallow placement of an implantable medical device against intercostal muscle tissue can be especially suitable to act as a wireless repeater between a deep-organ implant (e.g., implant located entirely within the heart) and other equipment, such as another implant or an extracorporeal medical device (e.g., programming device or data acquisition device).

The implantable medical device can attach to intercostal muscles (e.g., the tissue between individual ribs). The implantable medical device can sit flush against the ribcage and provide therapy to targeted tissue via a lead. Fixation against the intercostal muscles can provide a controlled and consistent implant depth. When an implantable medical device is anchored to the intercostal muscles, the ribcage can provide additional protection from external impacts and can immobilize the implantable medical device from movement, and thus reduce mechanical fatigue.

In some cases, the implantable medical device can be positioned adjacent implant sites such as compliant organs (e.g., organs that are not adversely affected by the implantable medical device) of the gut, such as adjacent the large intestine. Positioning the implantable medical device adjacent compliant organs can ensure that non-compliant organs are not disrupted by the implanted medical device, and thus minimize potential complications from implantation.

Elongated shaft(s) can extend from an underside (e.g., muscle-tissue-contacting side or anchoring surface) of the main body of the implantable medical device. In some cases, a single elongated shaft can extend from at or near a first edge of the main body. The elongated shaft can be oriented such that the second end of the elongated shaft is positioned above the tissue-contacting surface and an angle between the long axis of the elongated shaft and the tissue-contacting surface is an acute angle. The acute angle can be defined as an angle between the elongated shaft and an orthogonal projection of the elongated shaft onto the tissue-contacting surface.

In some cases, two or more elongated shafts (e.g., a first elongated shaft and a second elongated shaft) can extend from at or near a first edge of the main body and at an acute angle, which can be known as a common orientation. In some cases, the elongated shaft(s) include a shaft-connection site that is at or near the first end and that is coupled to a surface-connection site of the main body. In some cases, the main body can include one or more surface-connection sites at or near an edge of the main body. The surface-connection site is configured to couple the first end of the elongated to the main body via the shaft-connection site. In some cases where the elongated shaft(s) extend from at or near a first edge of the main body and at an acute angle with the long axis of the elongated shaft(s) and the tissue-contacting surface (e.g., in a common orientation), one or more suture holes or other secondary anchoring features located at or near a second edge of the main body opposite the first edge can provide temporary fixation to temporarily secure the implantable medical device against the muscle tissue. In some cases, one or more elongated shaft(s) can extend from at or near a first edge of the main body and at an acute angle with the long axis of the elongated shaft(s) and the tissue-contacting surface, and one or more additional elongated shaft(s) can extend from at or near a second edge of the main body opposite the first edge and at a second acute angle with the second long axis of the opposing elongated shaft and the tissue-contacting surface, which can be known as opposing orientation. In some cases where two or more elongated shafts are used, in any orientation, all shafts can have the same lengths or at least one shaft can have a different length. When multiple shafts are used in opposing orientation, it can be desirable to have the one or more elongated shafts extending from at or near a first edge of the main body all have a longer length than the one or more opposing elongated shafts extending from at or near a second edge of the main body. In this case, implantation of the implantable medical device can include initially piercing the muscle tissue with the longer elongated shafts before thereafter piercing the muscle tissue with the shorter, opposing elongated shafts.

In some aspects, the implantable medical device includes an opposing elongated shaft that can be coupled to the main body at or near the second edge of the main body. The opposing elongated shaft is oriented such that the distal end of the opposing elongated shaft can also be positioned above the tissue-contacting surface. In some cases, the opposing elongated shaft is orientated such that an angle between a second long axis of the opposing elongated shaft and the tissue-contacting surface is also an acute angle. In some cases, the elongated shaft and the opposing elongated shaft are oriented such that the long axis of the elongated shaft and the second long axis of the opposing elongated shaft are in a same plane.

The terminal end of the second end of an elongated shaft (e.g., end furthest from the main body) can be slightly sharpened or pointed. An anchoring feature can extend from the second end of the elongated shaft. In some cases, the anchoring feature is located at or near the second end of the elongated shaft. In some cases, the anchoring feature is located at or near a distal end of the opposing elongated shaft. The anchoring feature can be configured to taper from an enlarged portion to a sharp distal tip. The sharp distal tip can be further from the second end than the enlarged portion. The anchoring feature can have a larger cross section than other portions of the elongated shaft. Any dimension of the cross section (e.g., height, width, area) of the anchoring feature can be larger than the cross section of other portions of the elongated shaft. In some cases, the anchoring feature has a cross section that is larger than an average (e.g., median) cross section of the elongated shaft. In some cases, the anchoring feature can be ball-shaped or bulb-shaped. In some cases, a rounded ball-shaped or bulb-shaped anchoring feature can allow for explantation or removal of the elongated shaft from the muscle tissue without substantial damage to the muscle tissue. In some cases, the anchoring feature can be substantially flat or can be three-dimensional. In some cases, the elongated shaft and the anchoring feature are a contiguous feature.

An elongated shaft can be made of any suitable material, such as titanium, steel, MP35N (e.g., a nickel-cobalt-chromium-molybdenum alloy), platinum, hyperelastic materials (e.g., NiTi alloy also known as Nitinol), or other appropriate materials. The shafts can be made of any suitable material, such as metal, and can be coated or non-coated. An elongated shaft can have sufficient flexibility or elasticity to allow the elongated shaft to have a natural, deployed position and a compressed position.

In the deployed position, the elongated shaft can form an acute angle between the long axis of the elongated shaft and the tissue-contacting surface. In the compressed position, the elongated shaft can be pressed towards or against the main body (e.g., the tissue-contacting surface) of the implantable medical device. The implantable medical device can be placed within a trocar or cannula when in the compressed position. When the implantable medical device leaves the trocar or cannula, the elongated shaft(s) can naturally spring out to the deployed position. In the deployed position, the elongated shaft(s) can be appropriately angled (e.g., less than 90°) to pierce intercostal muscle tissue and anchor the main body of the implantable medical device against the intercostal muscle tissue.

In some cases, the implantable medical device can be placed within a delivery device (e.g., a delivery sheath) in the compressed position to deliver the implantable medical device. The delivery sheath is configured to compresses at least one elongated shaft towards or against the main body of the implantable medical device. The delivery sheath may comprise a removable material (e.g., peelable or absorbable material) that surrounds or covers at least the elongated shaft of the implantable medical device. In some cases, the implantable medical device is inserted into a protective delivery sheath which allows efficient delivery of the implantable medical device regardless of the orientation of the elongated shaft(s). In addition, use of the delivery sheath can prevent engagement of the tissue by the elongated shaft(s) until the sheath is removed or the implantable medical device is deployed from the sheath.

The delivery sheath is configured to compress the elongated shaft(s) towards or against the main body while the implantable medical device is guided to the implant site, e.g., intercostal muscle tissue. The delivery sheath at least partially wraps the implantable medical device. Once the implantable medical device is at or near the implant site, the delivery sheath can be removed to deploy the implantable medical device in a decompressed state. In some cases, the delivery sheath is a tubular sheath to maintain access to a common pathway for device implantation and manipulation. In some aspects, the delivery sheath includes a lumen that has a diameter large enough to deliver (e.g., eject) the implantable medical device from the delivery sheath to the implant site.

In some cases, the delivery sheath is made from one or more of an implantable grade resorbable or non-resorbable polymer and/or metal material. In some cases, the delivery sheath comprises one or more of polypropylene, polyester, nylon, polyether ether ketone (PEEK), polyurethane, polycarbonate, titanium, and stainless steel. In some aspects, the delivery sheath comprises a conforming sheath material that tightly surrounds the circumference of implantable medical device. For example, the inner diameter of the sheath should slightly greater than the outer diameter of the main body of the implantable medical device. During implantation of an implantable medical device having one or more elongated shafts, pressure can be applied at an appropriate angle to cause the elongated shaft(s) to pierce the muscle and press the implantable medical device flush against the ribcage. In some cases where a single elongated shaft is used or where multiple elongated shafts in common orientation are used, the implantation process can include applying pressure to pierce the muscle tissue and press the main body of the implantable medical device flush against the ribcage, after which a secondary anchor (e.g., suture) can be optionally installed. In some cases where multiple elongated shafts in opposing orientation are used, the implantation process can include applying pressure in a first direction to pierce a first elongated shaft into muscle tissue, continuing to apply pressure to displace the main body in the first direction, and then applying pressure in a second direction opposite the first direction to pierce a second elongated shaft into the muscle tissue and press the main body of the implantable medical device flush against the ribcage. Even when multiple elongated shafts in opposing orientation are used, secondary fixation can be optionally used to provide additional temporary fixation while the muscle tissue heals around the elongated shafts.

In some cases, the implantable medical device can include a secondary fixation feature, such as a suture hole. A suture passed through the suture hole and into the muscle tissue can be used to provide secondary fixation. Secondary fixation can be temporary, such as through the use of a resorbing suture (an absorbable biological material, e.g., collagen). Secondary fixation can be maintained for a period of time sufficient to allow the muscle tissue to substantially heal around the anchoring feature. Substantially healing around the anchoring fixture can mean that the muscle tissue has healed enough such that the implantable medical device remains flush with the muscle tissue during normal use. For example, sufficient scar tissue can build up around the anchoring features to lock the implantable medical device in place.

The main body of the implantable medical device can house any suitable control circuitry necessary to perform its desired functions. For example, control circuitry can include pulse generators, sensing equipment, processors, memory, power generation devices, power storage devices, power regulating circuitry, wireless communication circuitry, antennas, and any other suitable devices or circuitry.

In some cases, the present disclosure provides a method for implanting a medical device on an implant site. The method can include inserting an implantable medical device (e.g., according to any of the embodiments described herein) into a delivery sheath in a compressed state. In the compressed state, the elongated shaft(s) are compressed towards or against the main body. The delivery sheath at least partly wraps the implantable medical device.

The at least partly wrapped implantable medical device can be guided to an implant site. In some cases, the at least partly wrapped implantable medical device is guided to the implant using a catheter. Once the at least partly wrapped implantable medical device is guided to the implant site, the implantable medical device can be deployed from the delivery sheath. During deployment, the implantable medical device can be removed (e.g., ejected or pushed with pushing tool) from the delivery sheath to release the implantable medical device into a decompressed state. In the decompressed state, the elongated shaft is oriented such that the second end is positioned above the tissue-contacting surface and an angle between the long axis of the elongated shaft and the tissue-contacting surface is an acute angle. The elongated shaft can be inserted into the implant site such that the anchoring feature attaches to a portion of the implant site.

In some cases, the implantable medical device further includes an opposing elongated shaft that is coupled to the main body at or near the second edge of the main body. When the implantable medical device is in the decompressed state, a distal end of the opposing elongated shaft is positioned above the tissue-contacting surface at a second acute angle. In some cases, the method further includes inserting the opposing elongated shaft into the implant site. In some cases, the elongated shaft and the opposing elongated shaft are inserted into the implant site at different times. In some cases, the elongated shaft and the opposing elongated shaft are different lengths.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram depicting an implantable medical device 100 having a main body 102 with an elongated shaft 104 according to certain aspects of the present disclosure. The main body 102 can include a tissue-contacting surface 112 extending between a first edge 114 and a second edge 116 of the main body 102. A lead 122 can extend from the main body 102 and include a lead end 124 at or near the proximal end of the lead 122. The lead end 124 can include one or more electrodes or other equipment necessary to interact with targeted tissue. The lead 122 can be removable couplable to the main body 102 or can be permanently coupled to the main body 102. The lead 122 can couple to control circuitry 120 that is enclosed within the main body 102 to facilitate transmission of electrical signals between the control circuitry 120 and the lead end 124. In an example, the control circuitry 120 can include an electrical pulse generator and the lead 122 can facilitate transmission of electrical pulses from the control circuitry 120 to electrode(s) at the lead end 124, and thus into the targeted tissue.

An elongated shaft 104 can facilitate anchoring or fixing the main body 102 to desired anchoring tissue, such as intercostal muscle tissue. When the main body 102 is anchored or fixed to the desired anchoring tissue, the tissue-contacting surface 112 of the main body 102 can come into direct contact with the desired anchoring tissue. In some cases, the tissue-contacting surface 112 can be shaped or contoured to rest flush against the curved shaped of intercostal muscle tissue. In some cases, the tissue-contacting surface 112 can be convex in shape.

The elongated shaft 104 can extend from the main body 102 and over the tissue-contacting surface 112 at an acute angle 158 between the long axis of the elongated shaft 104 and the tissue-contacting surface 112. As used herein, the term "over the tissue-contacting surface" is to be read as extending above the tissue-contacting surface when the tissue-contacting surface is facing up, such as depicted in FIG. 1. The acute angle 158 can be greater than 0° and less than 90°. In some cases, the acute angle 158 is between 10° and 50°, between 20° and 40°, between 25° and 35°, or at or approximately 30°. The elongated shaft 104 can meet the main body 102 at a first end 108 (e.g., proximal end) of the elongated shaft 104 and extend towards a second end 110 (e.g., distal end). The elongated shaft 104 can be coupled to an outer case of the main body 102 or an interior frame member of the main body 102, or to a surface-connection site of the main body 102. An interior frame member can be any suitable structural support within the main body 102, including a substrate of a circuit board (e.g., control circuitry 120) or a separate structural support. The second end 110 of the elongated shaft 104 can be pointed, sharpened, or otherwise formed or treated to facilitate insertion of the elongated shaft 104 into muscle tissue. The elongated shaft 104 can have a length such that the second end 110 of the elongated shaft 104 falls between second edge 116 of the main body 102 and a halfway point between the first edge 114 and the second edge 116 of the main body 102. In some cases, the elongated shaft 104 can be longer or shorter, such as extending beyond the second edge 116 of the main body 102.

The elongated shaft 104 can include an anchoring feature 106. The anchoring feature 106 can be any feature suitable for inhibiting removal of the elongated shaft 104 from muscle tissue after muscle tissue begins to heal around the anchoring feature 106. The anchoring feature 106 can extend from the second end 110 of the elongated shaft 104. The anchoring feature 106 can be configured to taper from an enlarged portion to a sharp distal tip. In some cases, the sharp distal tip can be further from the second end 110 than the enlarged portion. In some cases, the anchoring feature 106 includes a portion of the elongated shaft 104 that is generally larger in one or more of thickness or width, than an average (e.g., median average) thickness or width of the elongated shaft 104. In some cases, the anchoring feature 106 can have a cross section, such as at its widest point, that is greater than an average (e.g., median average) cross section of the elongated shaft 104. In some cases, a cross section of the enlarged portion of the anchoring feature 106 can be larger than a median cross section of the elongated shaft 104. Any dimension of the cross section (e.g., height, width, area) of the anchoring feature 106 can be larger than the cross section of other portions of the elongated shaft 104. In some cases, the anchoring feature 106 can have a rounded shape to facilitate implantation and explantation of the elongated shaft 104. Examples of rounded shapes include spheres, semi-circles, ellipses, semi-ellipses, ellipsoids, semi-ellipsoids, and other complex shapes having few or no sharp corners. In some cases, where explantation is not a concern, the anchoring feature 106 can include non-rounded shapes, such as triangles, arrows, and other shapes having sharp edges or corners.

In some cases, the main body 102 can optionally include a secondary fixation feature 118. The secondary fixation feature 118 is a built-in location for facilitating fixation of the main body 102 against the desired anchoring tissue. The secondary fixation feature 118 can inhibit movement of the main body 102 in an explantation direction (e.g., a direction generally opposite the direction in which the elongated shaft 104 enters the desired anchoring tissue). The secondary fixation feature 118 can be sized to employ any suitable fixation technique, such as suturing, stapling, clamping, or other techniques. In some cases, it may be especially desirable to provide a secondary fixation feature 118 sized to employ a temporary fixation technique. In some cases, the secondary fixation feature 118 is a suture hole sized to accept a suture such that when a suture passing through the suture hole and the desired anchoring tissue is tied, the suture can prevent the main body 102 from moving in an explantation direction. In some cases, a temporary suture (e.g., an absorbable suture) can be used to provide secondary fixation for a period of time sufficient to allow the desired anchoring tissue to heal around the anchoring feature 106 of the elongated shaft 104.

Figure 2:
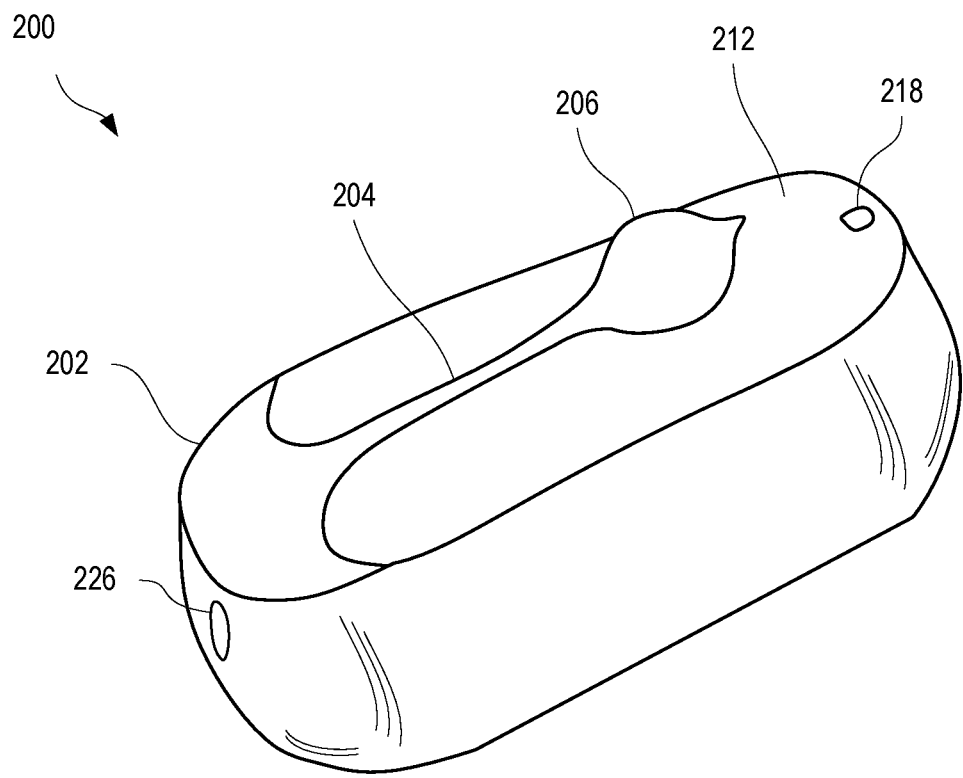
FIG. 2 is an axonometric diagram depicting an implantable medical device having a main body with an elongated shaft according to certain aspects of the present disclosure.

FIG. 2 is an axonometric diagram depicting an implantable medical device 200 having a main body 202 with an elongated shaft 204 according to certain aspects of the present disclosure. The main body 202 is shown having a generally rounded shape with few or no corners. The tissue-contacting surface 212 of the main body 202 has a convex shape that is designed to fit flush against intercostal muscle tissue. The elongated shaft 204 includes an anchoring feature 206 and a sharp distal end. The anchoring feature 206 has a rounded shape similar to a semi-circular shape. A suture hole 218 is depicted in the tissue-contacting surface 212.

Additionally, the main body 202 includes a lead port 226. The lead port 226 can accept a lead, such as lead 122 of FIG. 1. In some cases, instead of a lead port 226, a non-removable lead can extend directly from the main body 202, such as at the same location of lead port 226. The lead port 226 can be located in any suitable location. It can be desirable to locate the lead port 226 on an end of the main body 202, including the same end from which the elongated shaft 204 extends or the opposite end from which the elongated shaft 204 extends. When located on the same end from which the elongated shaft 204 extends, a lead extending from the lead port 226 can be inserted into the body cavity after the main body 202 has been inserted into the body cavity, potentially facilitating implantation. When located on the opposite end from which the elongated shaft 204 extends, a lead extending from the lead port 226 can minimize risk of explantation due to mechanical forces acting upon the lead during or after implantation.

Figure 3:
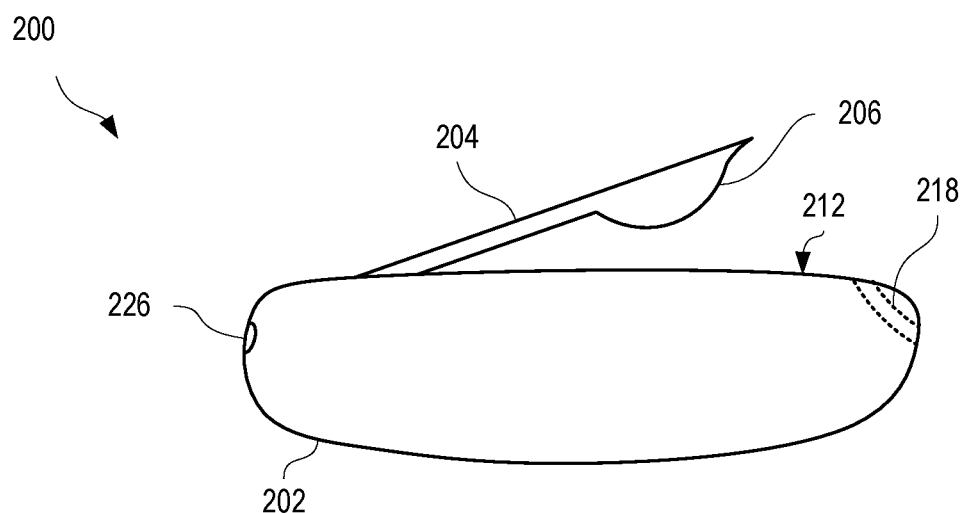
FIG. 3 is a side view of the implantable medical device of FIG. 2 according to certain aspects of the present disclosure.

FIG. 3 is a side view of the implantable medical device 200 of FIG. 2 according to certain aspects of the present disclosure. The elongated shaft 204 is depicted with an anchoring feature 206 having a rounded shape similar to a semi-circular shape. The elongated shaft 204 is depicted extending from at or near a first edge of the main body 202 and over the tissue-contacting surface 212 at an acute angle with the tissue-contacting surface 212 and the long axis of the elongated shaft 204. The suture hole 218 is seen passing through the main body 202 and exiting the tissue-contacting surface 212. The lead port 226 is shown at an end of the main body 202 opposite the suture hole 218, although the lead port 226 can be located in other places as well.

Figure 4:
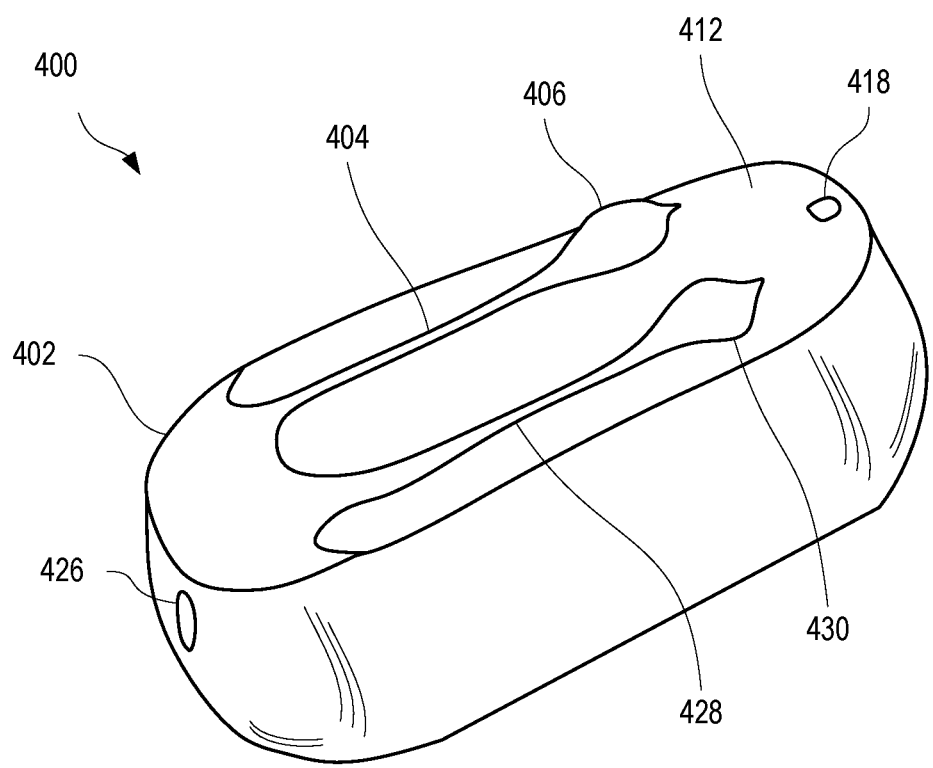
FIG. 4 is an axonometric diagram depicting an implantable medical device having a main body with first and second elongated shafts according to certain aspects of the present disclosure.

FIG. 4 is an axonometric diagram depicting an implantable medical device 400 having a main body 402 with first and second elongated shafts 404, 428 according to certain aspects of the present disclosure. The main body 402 is shown having a generally rounded shape with few or no corners. The tissue-contacting surface 412 of the main body 402 has a convex shape that is designed to fit flush against intercostal muscle tissue. A first elongated shaft 404 and a second elongated shaft 428 extend from the main body 402. Both the first and second elongated shafts 404, 428 extend from the main body 402 in a commonly oriented manner (e.g., both shafts extending from the same side of the main body 402). Both the first and second elongated shafts 404, 428 can extend over the tissue-contacting surface 412 at the same acute angle with the tissue-contacting surface 412, or at different acute angles with the tissue-contacting surface 412, with respect to the long axis of each of the first and second elongated shafts 404, 428. The first and second elongated shafts 404, 428 include respective anchoring features 406, 430 and respective sharp distal ends. Both anchoring features 406, 430 can have the same or different shapes. As depicted in FIG. 4, both anchoring features 406, 430 have rounded shapes similar to semi-circular shapes. A suture hole 418 is depicted in the tissue-contacting surface 412.

Additionally, the main body 402 includes a lead port 426, similar to lead port 226 of FIG. 2.

Figure 5:
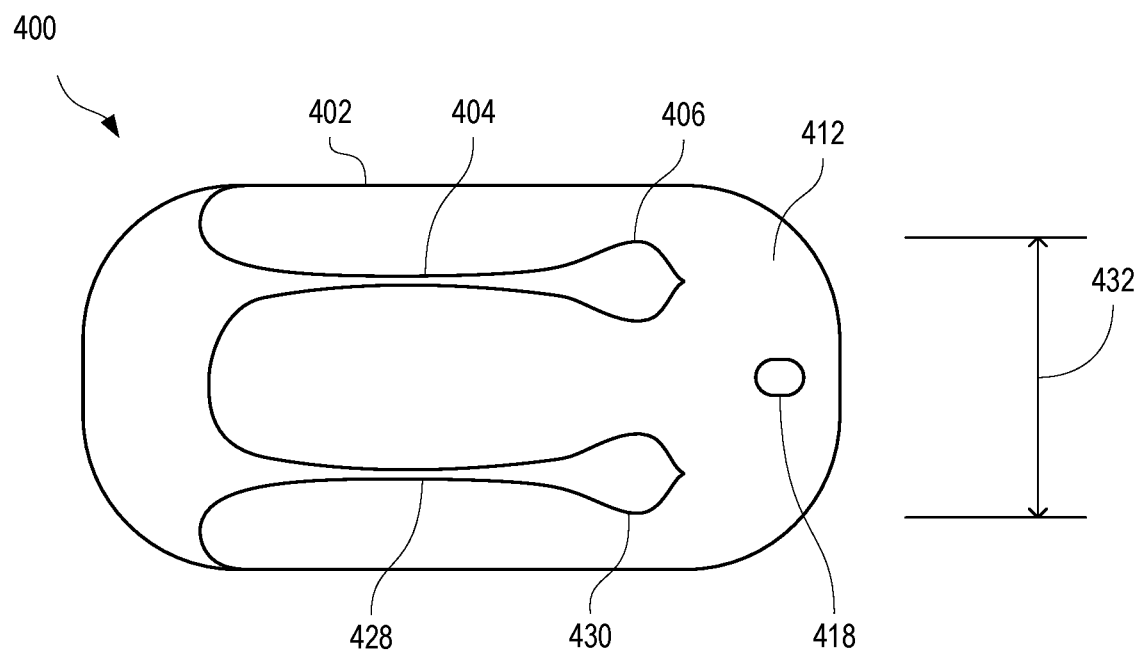
FIG. 5 is a top view of the implantable medical device of FIG. 4 according to certain aspects of the present disclosure.

FIG. 5 is a top view of the implantable medical device 400 of FIG. 4 according to certain aspects of the present disclosure. The first and second elongated shafts 404, 428 are depicted with respective anchoring features 406, 430 having rounded shapes similar to semi-circular shapes. Both elongated shafts 404, 428 are depicted extending in a commonly orientated fashion, extending from at or near a first edge of the main body 402 and over the tissue-contacting surface 412 at an acute angle with the tissue-contacting surface 412 and the long axis of the first and second elongated shafts 404, 428. The suture hole 418 is seen exiting the tissue-contacting surface 412.

When multiple elongated shafts (e.g., first and second elongated shafts 404, 428) are employed, a combined external width 432 of the elongated shafts can be defined as the widest distance between portions of the elongated shaft designed to penetrate the desired anchoring tissue. For example, as seen in FIG. 5, the combined external width 432 is the distance between the outermost edge of anchoring feature 406 (e.g., top edge as seen in FIG. 5) and the outermost edge of anchoring feature 430 (e.g., bottom edge as seen in FIG. 5). The combined external width 432 can be at least as small as the width of the desired anchoring tissue. For example, when the desired anchoring tissue is intercostal muscle tissue, the combined external width 432 can be at least as small as the intercostal space between adjacent ribs at the desired implant site. For example, combined external width 432 can be at or less than 20 mm, 19.5 mm, 19 mm, 18.5 mm, 18 mm, 17.5 mm, 17 mm, 16.5 mm, 16 mm, 15.5 mm, 15 mm, 14.5 mm, 14 mm, 13.5 mm, 13 mm, 12.5 mm, 12 mm, 11.5 mm, 11 mm, 10.5 mm, 10 mm, 9.5 mm, 9 mm, 8.5 mm, 8 mm, 7.5 mm, 7 mm, or 6.5 mm. In some cases, a patient's intercostal space at the desired implant site can be measured or estimated and an appropriately-sized intrathoracic, implantable medical device 400 having first and second elongated shafts 404, 428 with an appropriate combined external width 432 can be selected based on the patient's intercostal space measurement or estimate.

Figure 6:
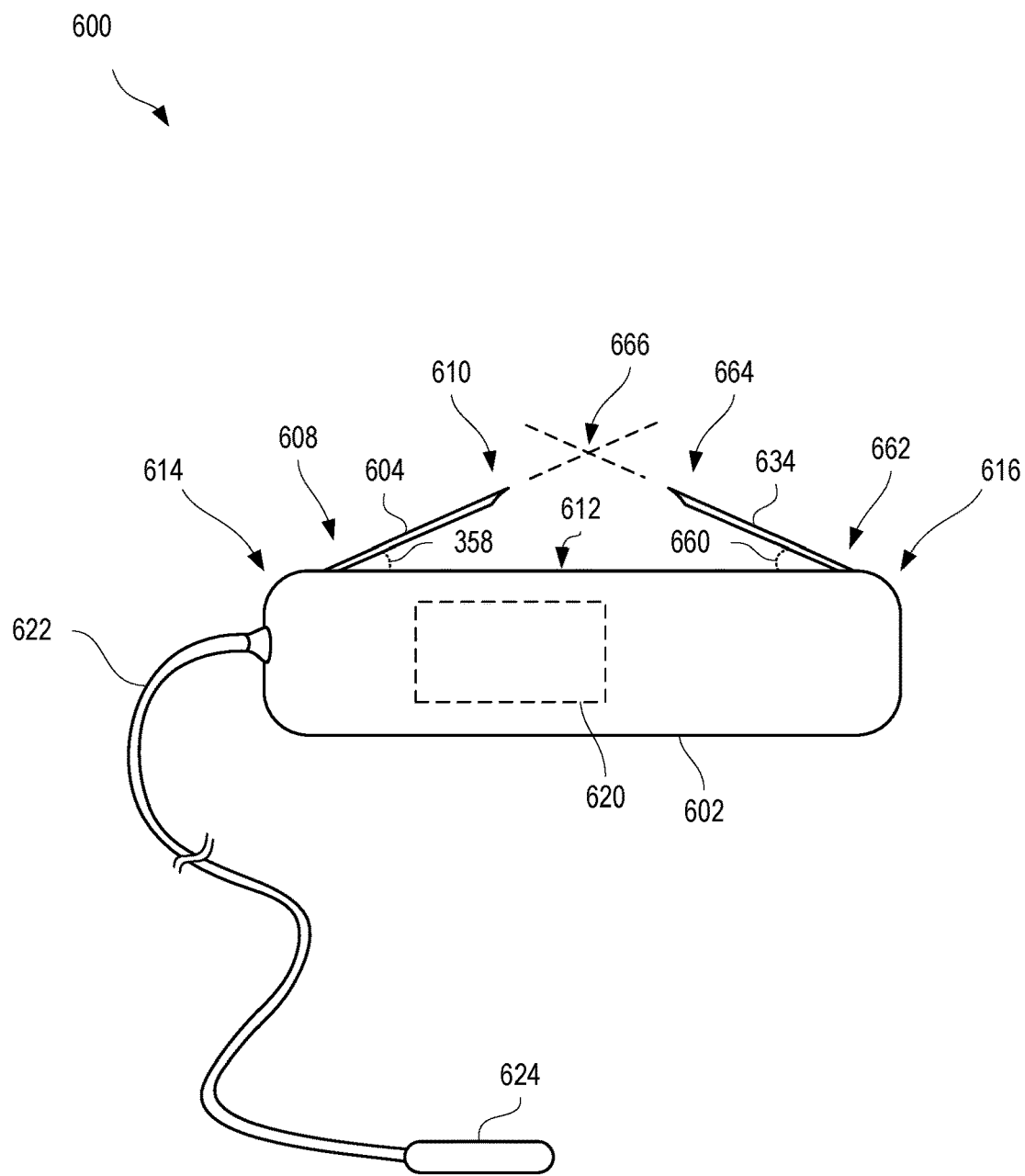
FIG. 6 is a schematic diagram depicting an implantable medical device having a main body with opposing elongated shafts according to certain aspects of the present disclosure.

FIG. 6 is a schematic diagram depicting an implantable medical device 600 having a main body 602 with opposing elongated shafts 604, 634 (first elongated shaft 604 and opposing elongated shaft 634) according to certain aspects of the present disclosure. The main body 602 can include a tissue-contacting surface 612 extending between a first edge 614 and a second edge 616 of the main body 602. A lead 622 can extend from the main body 602 and include a lead end 624 at or near the proximal end of the lead 622. The lead end 624 can include one or more electrodes or other equipment necessary to interact with targeted tissue. The lead 622 can be removable couplable to the main body 602 or can be permanently coupled to the main body 602. The lead 622 can couple to control circuitry 620 that is enclosed within the main body 602 to facilitate transmission of electrical signals between the control circuitry 620 and the lead end 624. In an example, the control circuitry 620 can include an electrical pulse generator and the lead 622 can facilitate transmission of electrical pulses from the control circuitry 620 to electrode(s) at the lead end 624, and thus into the targeted tissue.

A pair of opposing elongated shafts 604, 634 can facilitate anchoring or fixing the main body 602 to desired anchoring tissue, such as intercostal muscle tissue. When the main body 602 is anchored or fixed to the desired anchoring tissue, the tissue-contacting surface 612 of the main body 602 can come into direct contact with the desired anchoring tissue. In some cases, the tissue-contacting surface 612 can be shaped or contoured to rest flush against the curved shaped of intercostal muscle tissue. In some cases, the tissue-contacting surface 612 can be convex in shape.

Both of the opposing elongated shafts 604, 634 can extend from the main body 602 and over the tissue-contacting surface 612 at respective acute angles 658, 660 between the tissue-contacting surface 612 and the long axis of each respective opposing elongated shafts 604, 634. The acute angles 658, 660 can be greater than 0° and less than 90°. In some cases, the acute angles 658, 660 are between 10° and 50°, between 20° and 40°, between 25° and 35°, or at or approximately 30°. The acute angles 658, 660 can be the same angle or different angles.

Each elongated shaft 604, 634 can meet the main body 602 at respective first ends 608, 662 of the elongated shafts 604, 634 and extend towards respective second ends 610, 664 (e.g., distal ends). Each elongated shaft 604, 634 can include a shaft-connection site that is at or near first ends 608, 662. Each elongated shaft 604, 634 can be coupled to an outer case of the main body 602 or an interior frame member of the main body 602 or to a surface connection site of the main body 602. In some cases, the shaft-connection site of elongated shaft 604 is coupled to a surface-connection site positioned at or near the first edge 614 of the main body 602. In some cases, elongated shaft 634 (e.g., opposing elongated shaft) is coupled to a surface-connection site positioned at or near the second edge 616 of the main body 602. An interior frame member can be any suitable structural support within the main body 602, including a substrate of a circuit board (e.g., control circuitry 620) or a separate structural support. The second ends 610, 664 of the elongated shafts 604, 634 can be pointed, sharpened, or otherwise formed or treated to facilitate insertion of the elongated shafts 604, 634 into muscle tissue.

Elongated shaft 604 can extend from the main body 602 at a location at or near the first edge 614 of the main body 602. Opposing elongated shaft 634 can extend from the main body 602 at a location at or near the second edge 616 of the main body 602. Elongated shaft 604 and opposing elongated shaft 634 can extend generally towards one another, such that an imaginary line extending along the elongated shaft 604 and beyond its second end 610 intersects an imaginary line extending along the opposing elongated shaft 634 and beyond its distal end 664 at an imaginary point 666. The imaginary point 666 can be located at a distance spaced apart from the tissue-contacting surface 612. The elongated shafts 604, 634 can have lengths sufficient to provide a gap between second end 610 and distal end 664. In other words, the imaginary point 666 can be located in an imaginary plane perpendicular to the tissue-contacting surface 612 and perpendicular to another plane formed by the imaginary lines, wherein the imaginary plane is located between the second ends 610, 664 of the elongated shafts 604, 634. In some cases, the imaginary point 666 can be located approximately at a halfway point between the first edge 614 and the second edge 616 of the main body 602. In some cases, the imaginary point 666 can be located closer to the first edge 614 than the second edge 616 or closer to the second edge 616 than the first edge 614.

Each elongated shaft 604, 634 can have the same length or different lengths. In some cases, it can be desirable to have an elongated shaft 604 that is longer than the opposing elongated shaft 634, however in some cases it can be desirable to have an elongated shaft 604 that is shorter than the opposing elongated shaft 634.

In some cases, one or both of the elongated shafts 604, 634 can include an anchoring feature, such as anchoring feature 106 of FIG. 1. However, in some cases when elongated shafts 604, 634 are present in opposing orientation, adequate fixation may be achieved without the use of an anchoring feature.

In some cases, the main body 602 can optionally include a secondary fixation feature, such as secondary fixation feature 118 of FIG. 1. However, in some cases when elongated shafts 604, 634 are present in opposing orientation, adequate fixation may be achieved without the use of a secondary anchoring feature.

Figure 7:
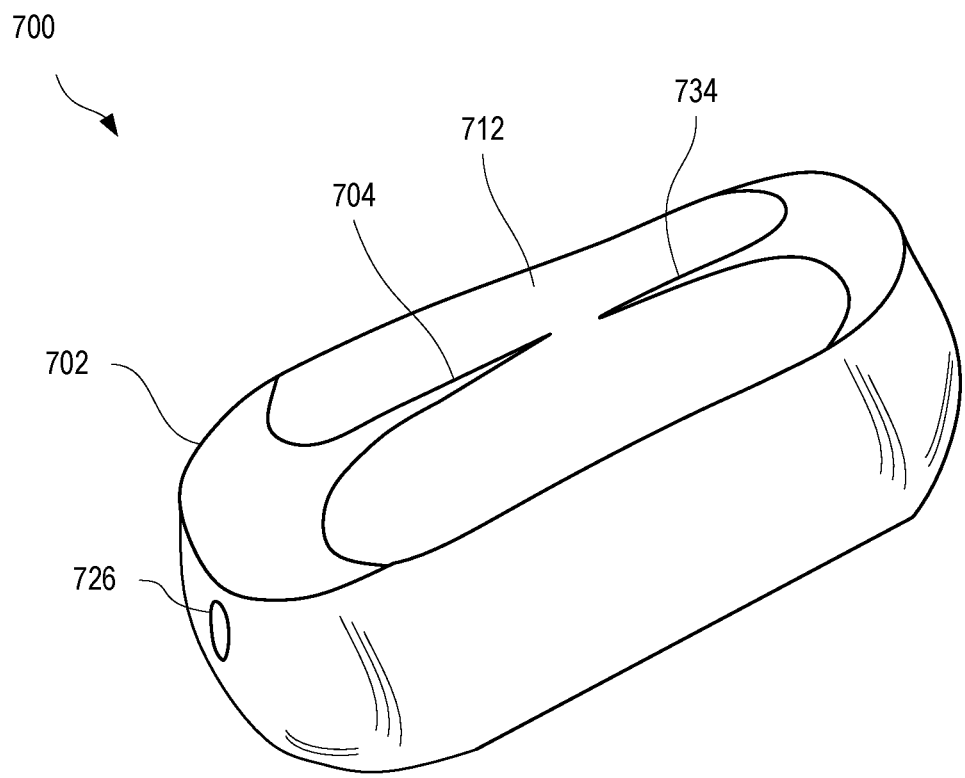
FIG. 7 is an axonometric diagram depicting an implantable medical device having a main body with opposing elongated shafts according to certain aspects of the present disclosure.

FIG. 7 is an axonometric diagram depicting an implantable medical device 700 having a main body 702 with opposing elongated shafts 704, 734 (e.g., elongated shaft 704 and opposing elongated shaft 734) according to certain aspects of the present disclosure. The main body 702 is shown having a generally rounded shape with few or no corners. The tissue-contacting surface 712 of the main body 702 has a convex shape that is designed to fit flush against intercostal muscle tissue. Elongated shaft 704 and opposing elongated shaft 734 extend from the main body 702. Elongated shafts 704 and opposing elongated shaft 734 extend from the main body 702 in an opposing orientation (e.g., both shafts extending from opposite edges of the main body 702 and generally towards one another). Both elongated shafts 704, 734 can extend over the tissue-contacting surface 712 at the same acute angle with the tissue-contacting surface 712, or at different acute angles with the tissue-contacting surface 712. Both elongated shafts 704, 734 are depicted devoid of anchoring features, although that need not be the case.

Additionally, the main body 702 includes a lead port 726, similar to lead port 226 of FIG. 2.

Figure 8:
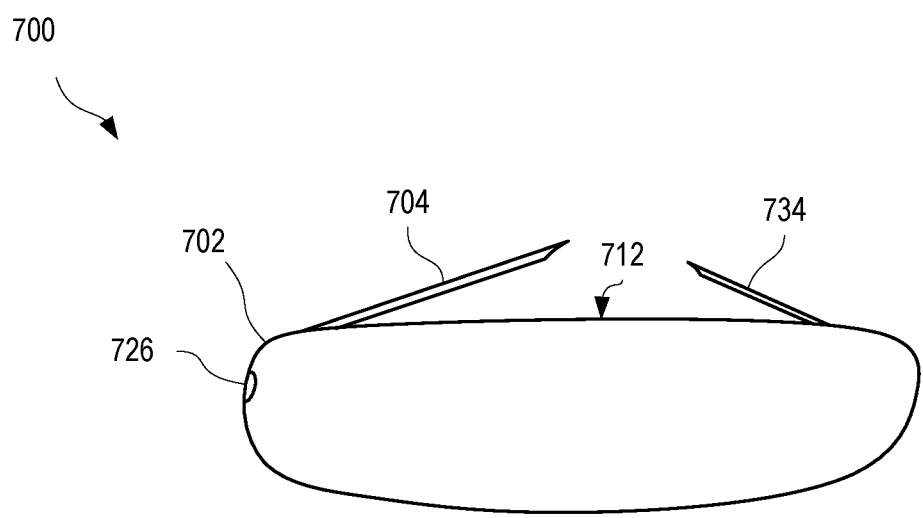
FIG. 8 is a side view of the implantable medical device of FIG. 7 according to certain aspects of the present disclosure.

FIG. 8 is a side view of the implantable medical device 700 of FIG. 7 according to certain aspects of the present disclosure. Elongated shaft 704 is depicted as being longer than opposing elongated shaft 734. Implantation can be facilitated by first inserting the longer elongated shaft (e.g., elongated shaft 704) into the muscle tissue before attempting to insert the shorter elongated shaft (e.g., opposing elongated shaft 734). Both elongated shafts 704, 734 are depicted extending in an opposing orientation, with each elongated shaft 704, 734 extending from adjacent respective first and second edges of the main body 702 and over the tissue-contacting surface 712 at respective acute angles with the tissue-contacting surface 712 (e.g., acute angle between the tissue-contacting surface 712 and the long axis of each respective elongated shaft 704, 734. The lead port 726 is depicted at a location adjacent where the larger of the two elongated shafts 704, 734 (e.g., elongated shaft 704) extends from the main body 702, however the lead port 726 can be located in other places as well.

Figure 9:
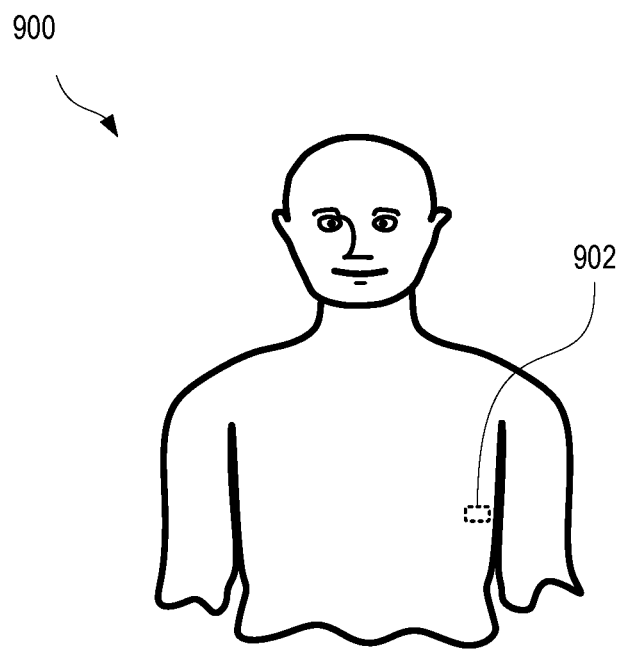
FIG. 9 is a front view of a patient depicting an implant site of an implantable medical device according to certain aspects of the present disclosure.

FIG. 9 is a front view of a patient 900 depicting an implant site 902 of an implantable medical device according to certain aspects of the present disclosure. The implant site 902 can be located within the thorax of the patient 900, and more specifically can be located within an intercostal space between ribs of the patient 900. In some cases, it can be desirable for the implant site 902 to be located laterally (e.g., not medially), with respect to the midsagittal plane of the body, within the thorax of the patient 900. However, the implant site 902 can be located medially or in any other suitable location.

Figure 10:
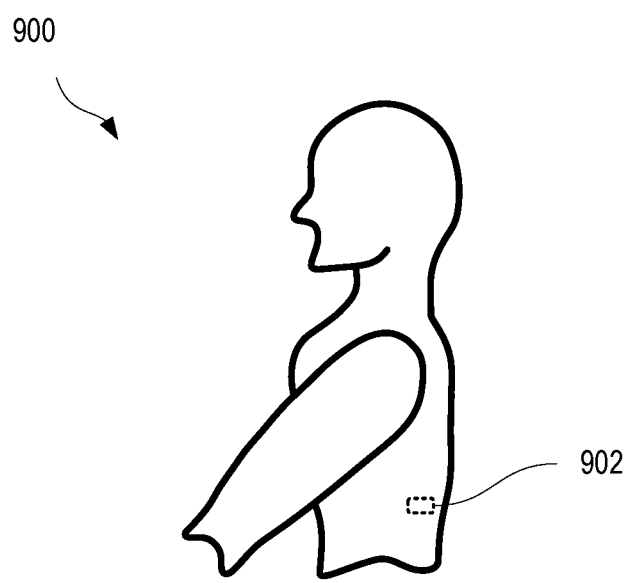
FIG. 10 is a side view of the patient of FIG. 9 depicting the implant site of the implantable medical device according to certain aspects of the present disclosure.

FIG. 10 is a side view of the patient 900 of FIG. 9 depicting the implant site 902 of the implantable medical device according to certain aspects of the present disclosure. The implant site 902 can be located within the thorax of the patient 900. In some cases, it can be desirable for the implant site 902 to be located dorsally (e.g., not ventrally), with respect to the sagittal plane of the body, within the thorax of the patient 900. However, the implant site 902 can be located ventrally or in any other suitable location. In an example, implant site 902 can be located laterally and dorsally at the intercostal region between the $2^{nd}$ and $3^{rd}$, $3^{rd}$ and $4^{th}$, $4^{th}$ and $5^{th}$, $5^{th}$ and $6^{th}$, $6^{th}$ and $7^{th}$, $7^{th}$ and $8^{th}$, $8^{th}$ and $9^{th}$, $9^{th}$ and $10^{th}$, $10^{th}$ and $11^{th}$ or $11^{th}$ and $12^{th}$ ribs.

Figure 11:
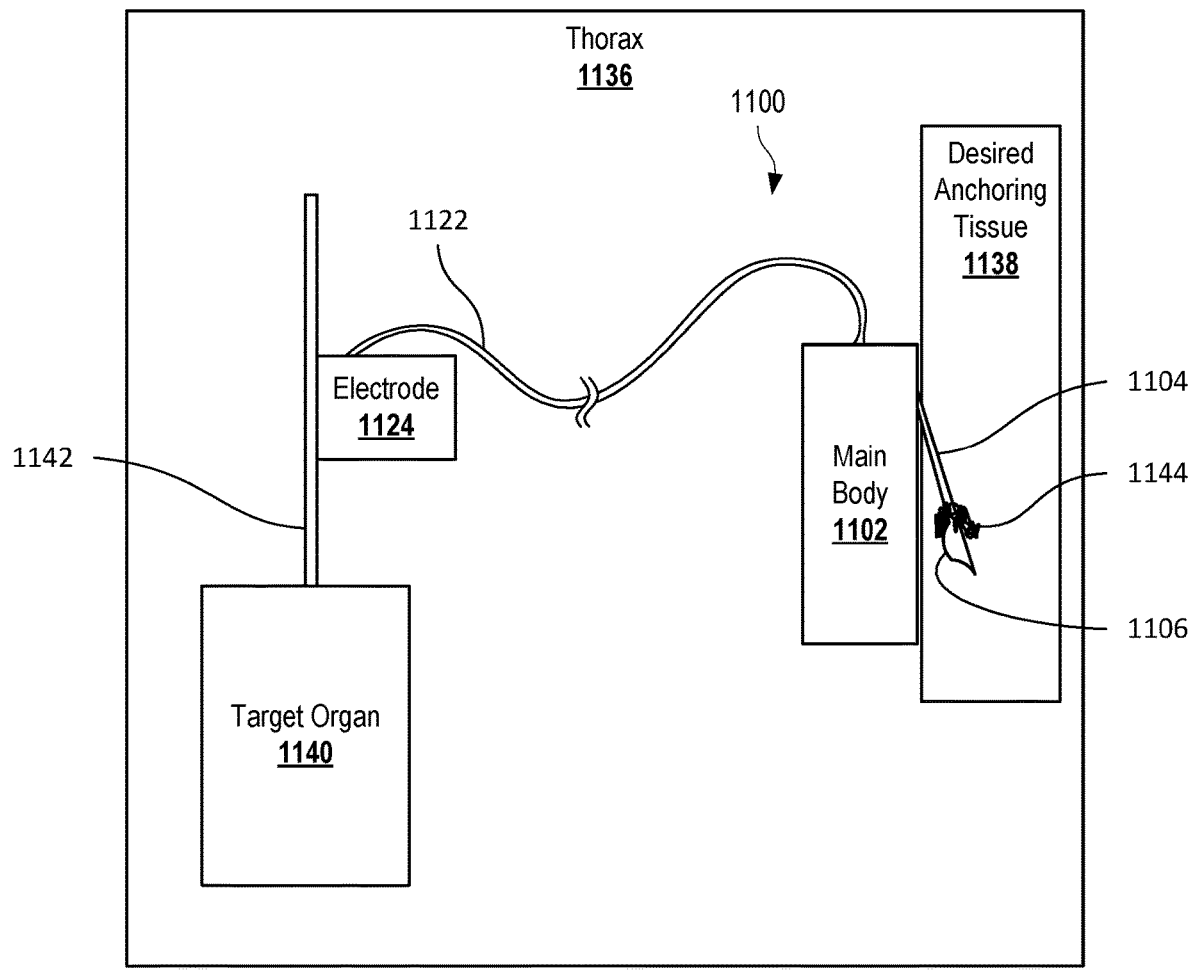
FIG. 11 is a schematic diagram depicting an implantable medical device implanted within a thorax according to certain aspects of the present disclosure.

FIG. 11 is a schematic diagram depicting an implantable medical device 1100 implanted within a thorax 1136 according to certain aspects of the present disclosure. The medical device 1100 can include a main body 1102 and an electrode 1124 coupled by a lead 1122. The lead 1122 can be of sufficient distance to allow the electrode 1124 to be placed at the targeted tissue when the main body 1102 is anchored to the desired anchoring tissue 1138.

As depicted in FIG. 11, the main body 1102 is anchored to the desired anchoring tissue 1138 (e.g., intercostal muscle tissue) via an elongated shaft 1104 having an anchoring feature 1106. The elongated shaft 1104 of FIG. 11 has been left inserted into the desired anchoring tissue 1138 for a sufficient period of time to allow buildup of scar tissue 1144 around the anchoring feature 1106, thus anchoring the main body 1102 to the desired anchoring tissue 1138 and inhibiting accidental explantation of the main body 1102.

The electrode 1124 can be positioned to target any desired target tissue. As seen in FIG. 11, the medical device 1100 is being used to treat a target organ 1140 (e.g., spleen) by placing the electrode 1124 on or adjacent a nerve bundle 1142 (e.g., one or more nerve cells) interacting with the target organ 1140. The electrode 1124 can sense electrical activity or deliver electrical pulses from or to the nerve bundle 1142, thus providing monitoring of or therapy to the target organ 1140. In some cases, electrical pulses delivered through electrode 1124 to the nerve bundle 1142 can promote or inhibit action potentials directed to the target organ 1140, and thus control function of the target organ 1140. In some cases, electrical pulses delivered through electrode 1124 to the nerve bundle 1142 can promote or inhibit action potentials directed from the target organ 1140, and thus control functions of the body indirectly related to the target organ 1140.

In some cases, electrode 1124 can be replaced with any suitable input or output device for providing monitoring or control to body tissue. Examples of suitable replacements can include chemical releasing agents, chemical sensors, light emitting devices, light sensors, mechanical devices, mechanical sensors, auditory devices, or any other appropriate device.

Figure 12:
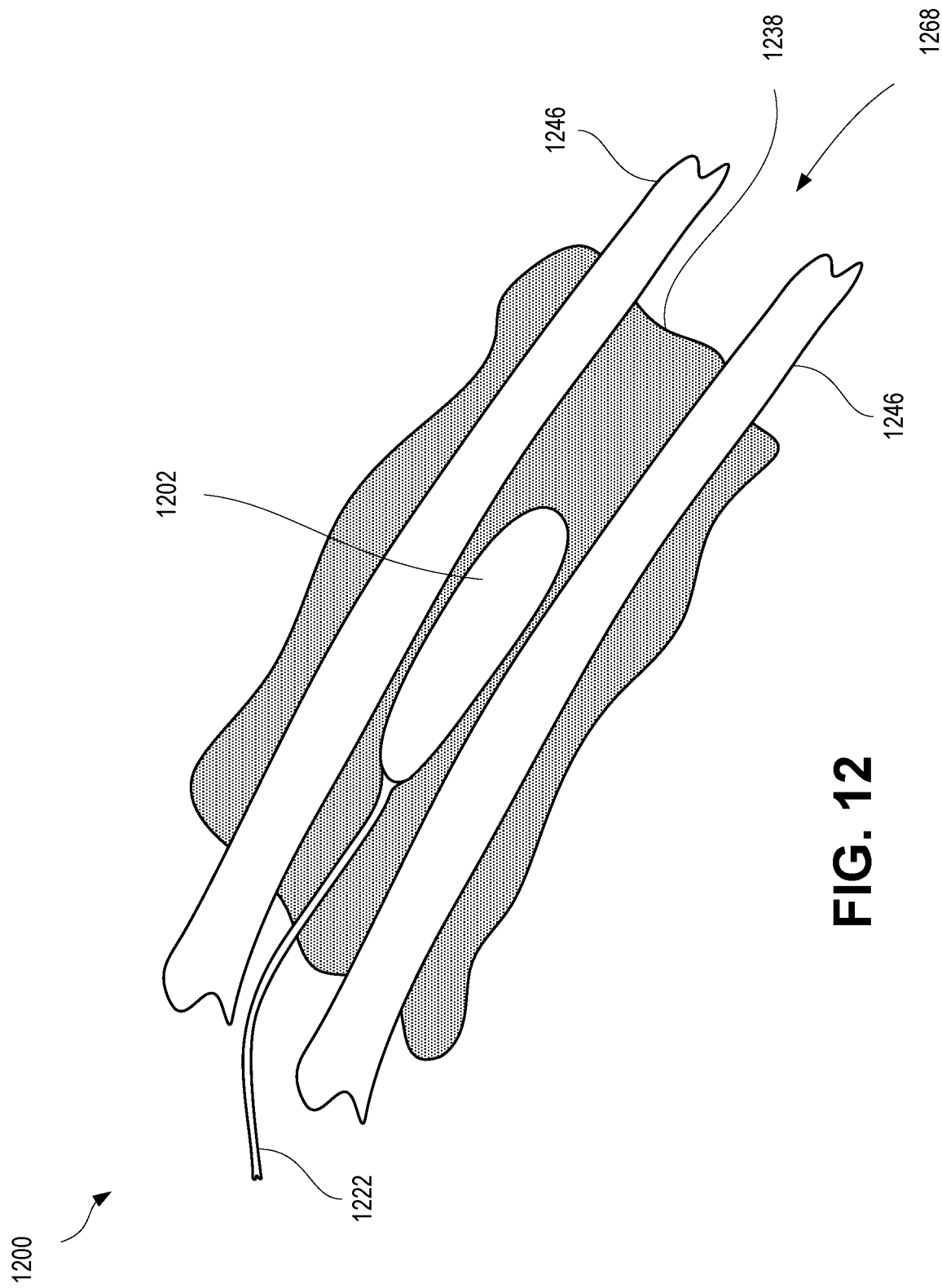
FIG. 12 is a front view depicting an implantable medical device implanted in an intercostal space between a pair of ribs according to certain aspects of the present disclosure.

FIG. 12 is a front view depicting an implantable medical device 1200 implanted in an intercostal space 1268 between a pair of ribs 1246 according to certain aspects of the present disclosure. The medical device 1200 can include a main body 1202 and a lead 1222. The main body 1202 can be anchored into the intercostal muscle tissue 1238 located within the intercostal space 1268 between a pair of ribs 1246. The main body 1202 can be anchored within the intercostal space 1268 between any suitable pair of ribs 1246, including at least between the $2^{nd}$ and $3^{rd}$, $3^{rd}$ and $4^{th}$, $4^{th}$ and $5^{th}$, $5^{th}$ and $6^{th}$, $6^{th}$ and $7^{th}$, $7^{th}$ and $8^{th}$, $8^{th}$ and $9^{th}$, $9^{th}$ and $10^{th}$, $10^{th}$ and $11^{th}$, or $11^{th}$ and $12^{th}$ ribs.

Figure 13:
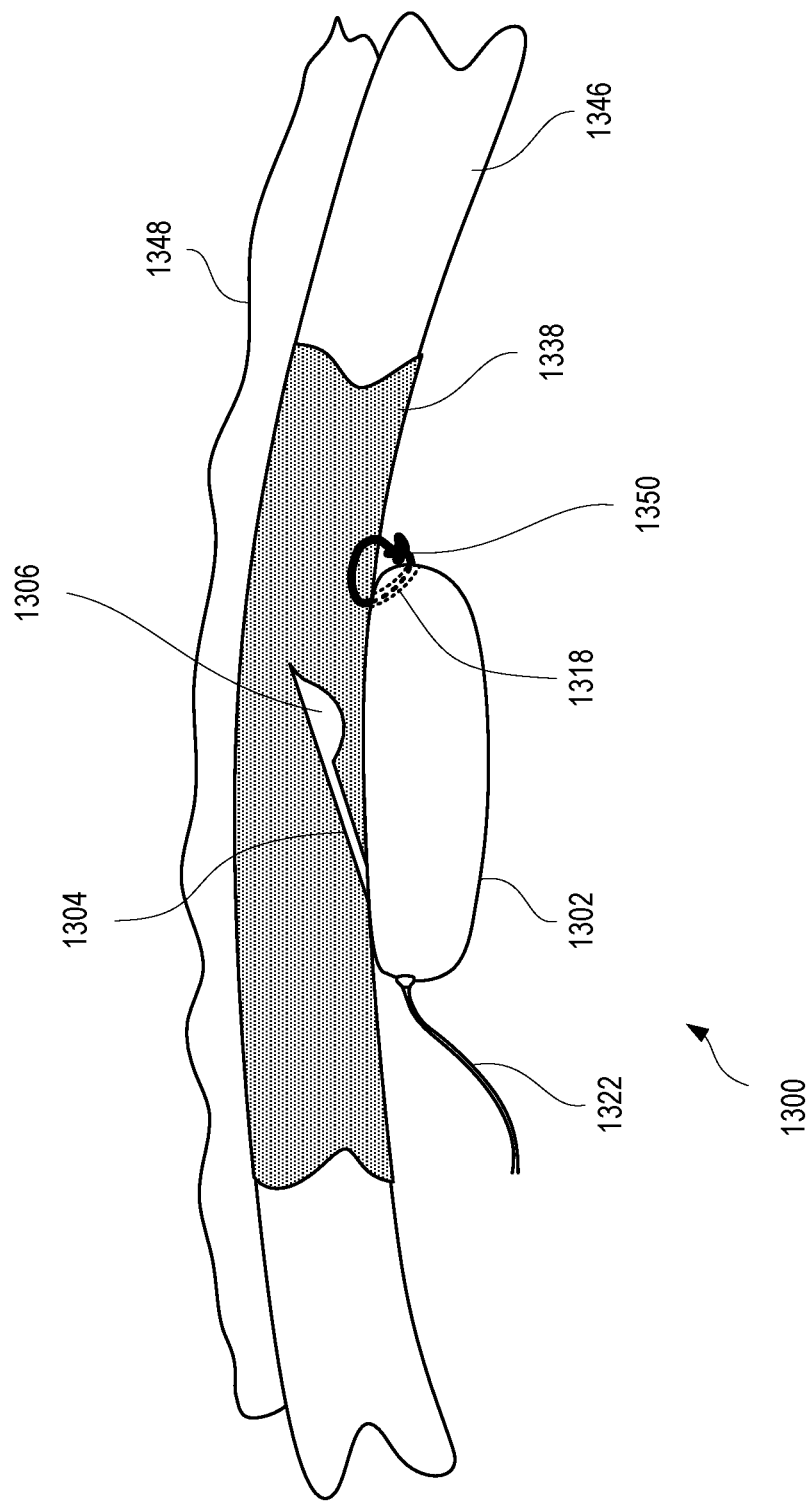
FIG. 13 is a partial cutaway top view depicting an implantable medical device implanted in an intercostal space between a pair of ribs according to certain aspects of the present disclosure.

FIG. 13 is a partial cutaway top view depicting an implantable medical device 1300 implanted in an intercostal space between a pair of ribs 1346 according to certain aspects of the present disclosure. The partial cutaway is taken within the intercostal space between the ribs 1346, similar to the intercostal space 1268 between ribs 1246 of FIG. 12. The medical device 1300 includes a main body 1302 and a lead 1322. The main body 1302 is shown with a convex tissue-contacting surface that rests flush against the intercostal muscle tissue 1338 between the ribs 1346. An elongated shaft 1304 extends from the main body 1302 and includes an anchoring feature 1306. The elongated shaft 1304 is shown inserted into the intercostal muscle tissue 1338. Additionally, a suture 1350 provides secondary fixation by being passed through a suture hole 1318 of the main body 1302 and the intercostal muscle tissue 1338. As seen in FIG. 13, the intercostal muscle tissue 1338 has not been provided sufficient time to heal and form scar tissue around the anchoring feature 1306 of the elongated shaft 1304, however the suture 1350 can provide sufficient secondary fixation for a duration suitable for sufficient scar tissue to form around the anchoring feature 1306. The suture 1350 can be an absorbable suture designed to be absorbed after sufficient scar tissue has formed around the anchoring feature 1306.

Due to the placement of the main body 1302 flush or nearly flush against the intercostal muscle tissue 1338 in the intercostal space between the ribs 1346, the main body 1302 can rest substantially near the exterior surface of the skin 1348 of the patient. Thus, the main body 1302 is able to rest at a relatively shallow depth below the surface of the skin 1348 and therefore provide wireless communication without the need for high power draw and large antennas.

FIG. 14 is a front view depicting an implantation kit 1400 containing an implantable medical device 1402 with an elongated shaft 1404 in a compressed position within a trocar 1452 according to certain aspects of the present disclosure. When the medical device 1402 (e.g., the main body of the medical device 1402) is placed within the inner diameter of the trocar 1452, the elongated shaft 1404 can be moved to a compressed position. In the compressed position, the elongated shaft 1404 can be urged towards the main body of the medical device 1402 (e.g., towards the tissue-contacting surface of the main body). In some cases, implantable medical device 1402 is in a compressed position within a delivery sheath.

FIG. 15 is a front view depicting the implantation kit 1400 of FIG. 14 with the elongated shaft 1404 in a deployed position after exiting the trocar 1452 according to certain aspects of the present disclosure. When the medical device 1402 (e.g., the main body of the medical device 1402) has exited the trocar 1452, the elongated shaft 1404 can naturally urge itself towards the deployed position, in which the elongated shaft 1404 is ready for insertion into the desired anchoring tissue.

Figure 16:
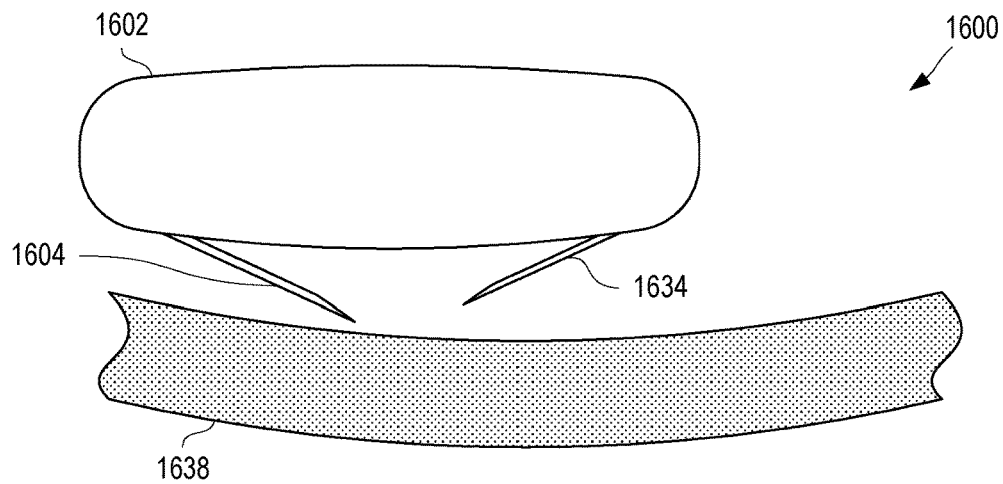
FIG. 16 is a side view depicting an implantable medical device prior to implantation in muscle tissue according to certain aspects of the present disclosure.

FIG. 16 is a side view depicting an implantable medical device 1600 prior to implantation in muscle tissue 1638 according to certain aspects of the present disclosure. The main body 1602 of the medical device 1600 can be placed adjacent the muscle tissue 1638. The medical device 1600 can include an elongated shaft 1604 and an opposing elongated shaft 1634. The elongated shaft 1604 can be longer than the opposing elongated shaft 1634.

Figure 17:
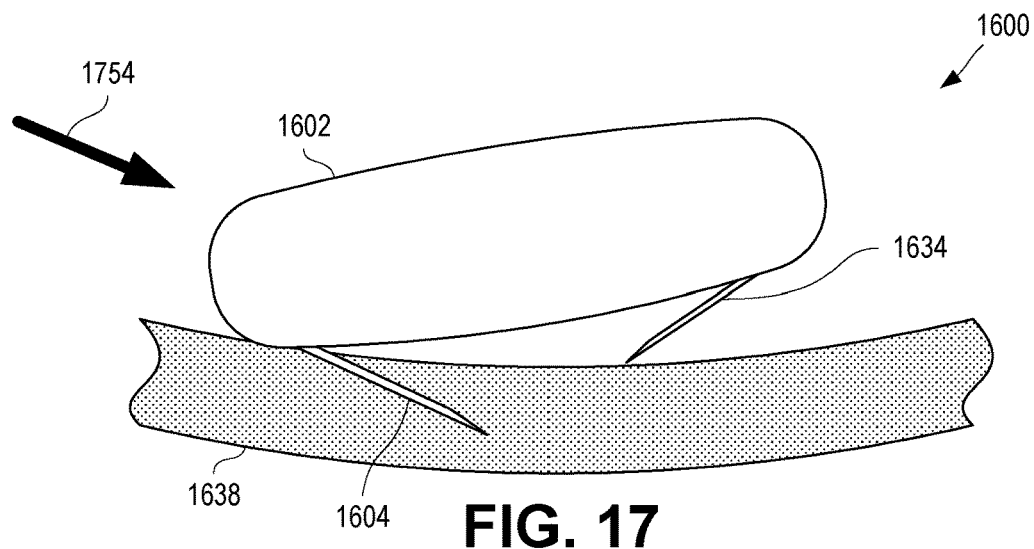
FIG. 17 is a side view depicting the implantable medical device of FIG. 16 during a first stage of implantation according to certain aspects of the present disclosure.

FIG. 17 is a side view depicting the implantable medical device 1600 of FIG. 16 during a first stage of implantation according to certain aspects of the present disclosure. In some cases, before the first stage of implantation, the implantable medical device can be inserted into a delivery sheath in a compressed state. In the compressed state, the elongated shaft(s) are compressed towards or against the main body. The delivery sheath at least partly wraps the implantable medical device. The at least partly wrapped implantable medical device can be guided to an implant site.

Once the at least partly wrapped implantable medical device is guided to the implant site, the implantable medical device can be deployed from the delivery sheath. During deployment, the implantable medical device can be removed (e.g., ejected or pushed with pushing tool) from the delivery sheath to release the implantable medical device into a decompressed state. In the decompressed state, the elongated shaft is oriented such that the second end is positioned above the tissue-contacting surface and an angle between the long axis of the elongated shaft and the tissue-contacting surface is an acute angle.

When in the first stage of implantation, the elongated shaft 1604 can be inserted into the muscle tissue 1638 by applying force to the main body 1602 in a first direction 1754. In some cases, the main body 1602 can be tilted to move the opposing elongated shaft 1634 away from the surface of the muscle tissue 1638.

Figure 18:
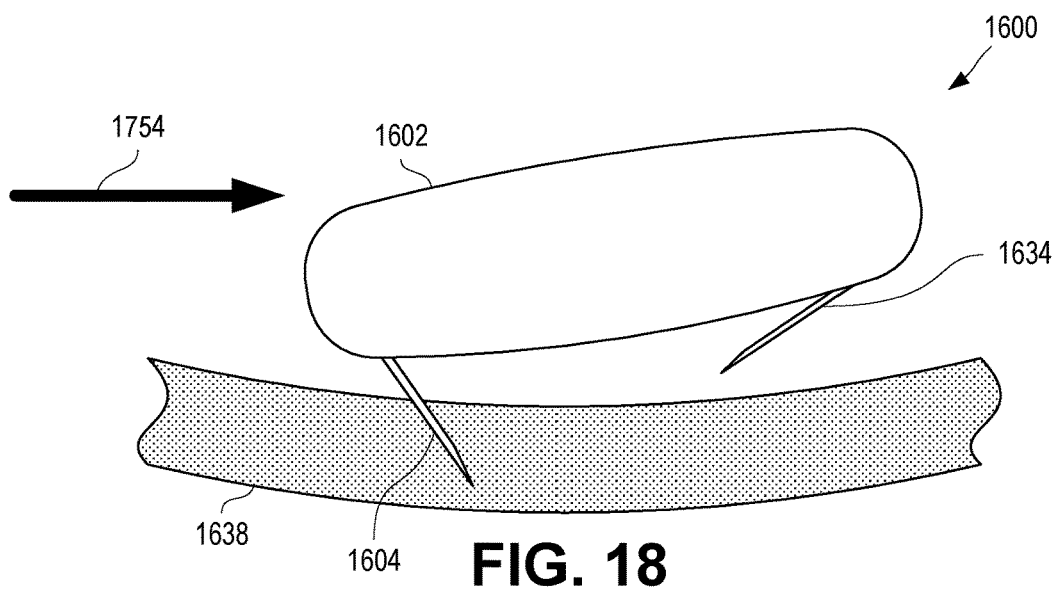
FIG. 18 is a side view depicting the implantable medical device of FIG. 16 during a second stage of implantation according to certain aspects of the present disclosure.

FIG. 18 is a side view depicting the implantable medical device 1600 of FIG. 16 during a second stage of implantation according to certain aspects of the present disclosure. When in the second stage, the elongated shaft 1604 within the muscle tissue 1638 can be forced further in the first direction 1754, thus stretching the muscle tissue 1638 near elongated shaft 1604. In some cases, the elongated shaft 1604 can flex to facilitate displacement of the main body 1602 in the first direction 1754. The required force can be achieved by pushing or pulling on main body 1602 in the first direction 1754. In some cases, the main body 1602 can be lifted or tilted to move the opposing elongated shaft 1634 away from the surface of the muscle tissue 1638.

Figure 19:
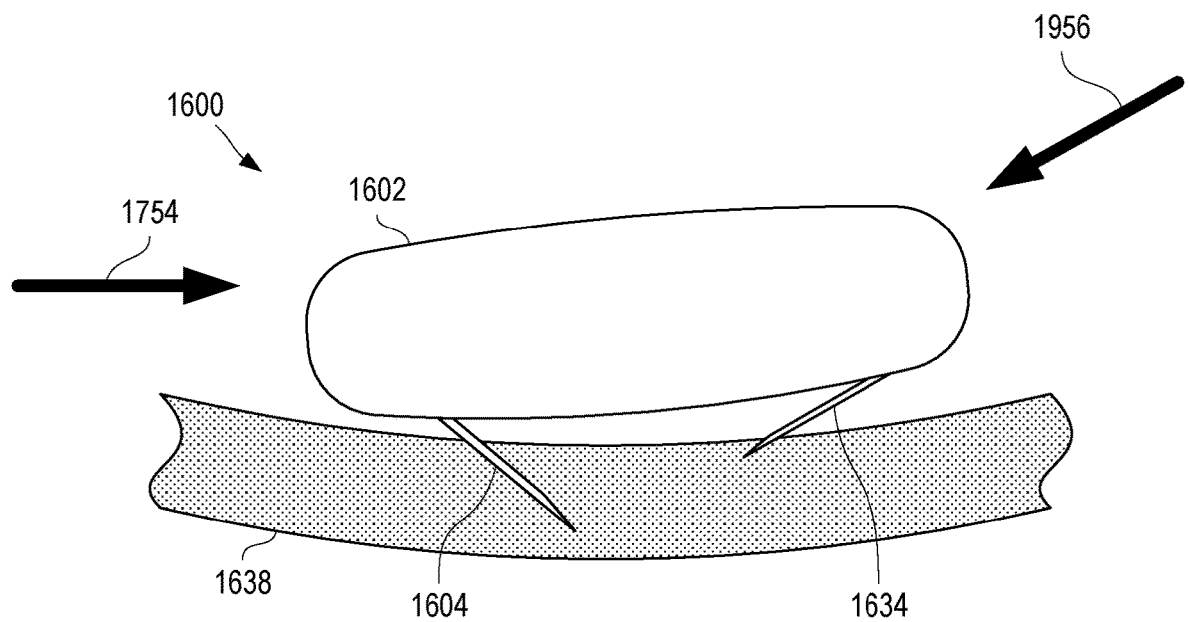
FIG. 19 is a side view depicting the implantable medical device of FIG. 16 during a third stage of implantation according to certain aspects of the present disclosure.

FIG. 19 is a side view depicting the implantable medical device 1600 of FIG. 16 during a third stage of implantation according to certain aspects of the present disclosure. When in the third stage, the muscle tissue 1638 near elongated shaft 1604 has been stretched and in some cases elongated shaft 1604 has flexed to facilitate displacement of the main body 1602 in the first direction 1754. In the third stage, the main body 1602 is allowed to move in the second direction 1956 (e.g., opposite the first direction 1754) as the opposing elongated shaft 1634 is inserted into the muscle tissue 1638.

Figure 20:
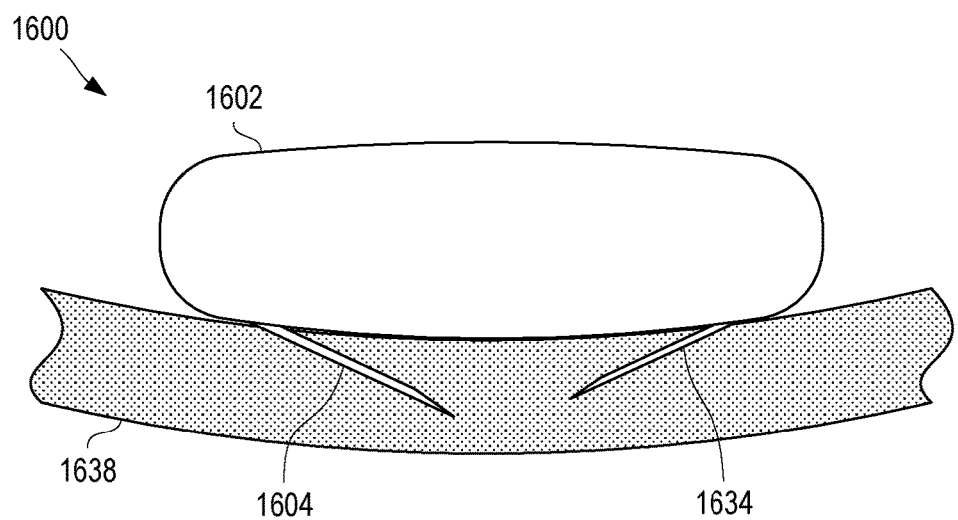
FIG. 20 is a side view depicting the implantable medical device of FIG. 16 as implanted into muscle tissue according to certain aspects of the present disclosure.

FIG. 20 is a side view depicting the implantable medical device 1600 of FIG. 16 as implanted into muscle tissue according to certain aspects of the present disclosure. After successful implantation, the main body 1602 of the medical device 1600 can rest flush or nearly flush against the muscle tissue 1638. Due to the stretching of the muscle tissue 1638 and/or flexing of the elongated shaft 1604 prior to insertion of the opposing elongated shaft 1634, sufficient tension exists between the elongated shafts 1604, 1634 (e.g., due to natural spring bias of the elongated shaft 1604 and/or springy nature of the stretched muscle tissue 1638) to keep the main body 1602 anchored against the muscle tissue 1638. The main body 1602 can be especially anchored from movement in either the first direction 1754 or the second direction 1956.

Thereafter, if explantation of the medical device 1600 is desired, the main body 1602 can be explanted through force being applied to the main body 1602 in a direction away from the muscle tissue 1638 in amounts sufficient to stretch the muscle tissue 1638 and/or flex one or both of the elongated shafts 1604, 1634 to a point where the elongated shafts 1604, 1634 withdraw from the muscle tissue 1638.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

The invention claimed is:

1. An implantable medical device, comprising:
   a main body having a tissue-contacting surface comprising a first edge, the tissue-contacting surface of the main body having a convex shape;
   an elongated shaft having a long axis that extends from a proximal end of the elongated shaft to a distal end of the elongated shaft, wherein the elongated shaft includes a shaft-connection site that is at or near the proximal end and that is coupled to a surface-connection site of the main body, the surface-connection site of the main body being at or near the first edge of the main body, wherein the elongated shaft is oriented such that:
      the elongated shaft is over the tissue-contacting surface; and
      an angle between the long axis of the elongated shaft and the tissue-contacting surface is an acute angle; and
   an anchoring feature adjacent the distal end of the elongated shaft, the anchoring feature being configured to taper from an enlarged portion to a sharp distal tip at the distal end of the elongated shaft, and a cross sectional area of the enlarged portion of the anchoring feature being larger than a median-cross sectional area of the elongated shaft,
   wherein the enlarged portion comprises a top region and a bottom region, the top region comprises a flat portion that terminates at the sharp distal tip, and the bottom region comprises a bulbous portion protruding away from the flat portion.

2. The device of claim 1, wherein the acute angle is between 10° and 50°.

3. The device of claim 1, further comprising:
   an opposing elongated shaft that is coupled to the main body at or near a second edge of the main body.

4. The device of claim 3, wherein a distal end of the opposing elongated shaft is over the tissue-contacting surface.

5. The device of claim 3, wherein a second angle between a second long axis of the opposing elongated shaft and the tissue-contacting surface is also an acute angle.

6. The device of claim 3, wherein the opposing elongated shaft is shorter than the elongated shaft.

7. The device of claim 3, wherein the elongated shaft and the opposing elongated shaft are oriented such that the long axis of the elongated shaft and a second long axis of the opposing elongated shaft are in a same plane.

8. The device of claim 3, wherein the opposing elongated shaft also includes an anchoring feature that tapers from an enlarged portion to a sharp distal tip.

9. The device of claim 1, further comprising:
   a second elongated shaft that is coupled to the main body at or near the first edge of the main body.

10. The device of claim 9, wherein a second long axis of the second elongated shaft is parallel to the long axis of the elongated shaft.

11. The device of claim 9, wherein a widest distance between the elongated shaft and the second elongated shaft is less than 18 mm.

12. The device of claim 1, wherein the main body further comprises control circuitry for generating an electrical stimulus.

13. The device of claim 12, further comprising a lead coupled to the control circuitry of the main body and configured to transmit electrical signals at a distal portion of the lead.

14. The device of claim 1, wherein the elongated shaft and the anchoring feature are contiguous.

15. A system comprising:
   the implantable medical device of claim 1; and
   a delivery sheath that surrounds a circumference of the implantable medical device.

16. A method of implanting a medical device, the method comprising:
   inserting an implantable medical device into a delivery sheath in a compressed state such that the implantable medical device is at least partly wrapped, the implantable medical device comprising:
      a main body having a tissue-contacting surface comprising a first edge and a second edge, the tissue-contacting surface of the main body having a convex shape;
      an elongated shaft having a long axis that extends from a proximal end of the elongated shaft to a distal end of the elongated shaft, wherein the proximal end is adjacent to the main body and the distal end is further from the main body than the proximal end, wherein the elongated shaft includes a shaft-connection site that is at or near the proximal end and that is coupled to a surface-connection site of the main body, the surface-connection site of the main body being at or near the first edge of the main body; and
      an anchoring feature adjacent the distal end of the elongated shaft, the anchoring feature being configured to taper from an enlarged portion to a sharp distal tip at the distal end of the elongated shaft, and a cross sectional area of the enlarged portion of the anchoring feature being larger than a median cross sectional area of the entire elongated shaft,
      wherein the enlarged portion comprises a top region and a bottom region, the top region comprises a flat portion that terminates at the sharp distal tip, and the bottom region comprises a bulbous portion protruding away from the flat portion;

guiding the at least partly wrapped implantable medical device to an implant site;

deploying the implantable medical device from the delivery sheath, wherein deploying includes releasing the implantable medical device into a decompressed state, such that the elongated shaft is oriented such that:

the elongated shaft is over the tissue-contacting surface; and an angle between the long axis of the elongated shaft and the tissue-contacting surface is an acute angle, wherein the elongated shaft extends from the first edge of the main body towards the second edge of the main body; and inserting the elongated shaft into the implant site such that the anchoring feature attaches to a portion of the implant site.

17. The method of claim 16, wherein:

the implantable medical device further includes an opposing elongated shaft that is coupled to the main body at or near the second edge of the main body; and when the implantable medical device is in the decompressed state, a distal end of the opposing elongated shaft is over the tissue-contacting surface at a second acute angle.

18. The method of claim 17, further comprising inserting the opposing elongated shaft into the implant site.

19. The method of claim 17, wherein the elongated shaft and the opposing elongated shaft are inserted into the implant site at different times.

20. The method of claim 17, wherein the elongated shaft and the opposing elongated shaft are different lengths.

* * * * *